United States Patent
Sousa et al.

(10) Patent No.: US 10,451,563 B2
(45) Date of Patent: Oct. 22, 2019

(54) INSPECTION OF PHOTOMASKS BY COMPARING TWO PHOTOMASKS

(71) Applicant: KLA-Tencor Corporation, Milpitas, CA (US)

(72) Inventors: Weston L. Sousa, San Jose, CA (US); Yalin Xiong, Pleasanton, CA (US); Carl E. Hess, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 147 days.

(21) Appl. No.: 15/438,588

(22) Filed: Feb. 21, 2017

(65) Prior Publication Data

US 2018/0238816 A1    Aug. 23, 2018

(51) Int. Cl.
*G03F 1/84* (2012.01)
*G01N 21/956* (2006.01)
*G01N 21/88* (2006.01)
*G06T 7/00* (2017.01)

(52) U.S. Cl.
CPC ... *G01N 21/95607* (2013.01); *G01N 21/8851* (2013.01); *G03F 1/84* (2013.01); *G06T 7/001* (2013.01); *G01N 2021/8887* (2013.01); *G01N 2021/95676* (2013.01); *G06T 2207/10061* (2013.01); *G06T 2207/30148* (2013.01)

(58) Field of Classification Search
CPC ......... G01N 21/95607; G01N 21/8851; G01N 21/956; G01N 21/93; G01N 2021/95676; G01N 2021/8887; G01N 2021/95615; G06T 7/001; G06T 2207/30148; G06T 2207/20224

USPC .......................................................... 382/149
See application file for complete search history.

(56) References Cited

U.S. PATENT DOCUMENTS

| | | | |
|---|---|---|---|
| 4,209,257 A | 6/1980 | Uchiyama | |
| 5,572,598 A * | 11/1996 | Wihl | G01N 21/95607 356/398 |
| 6,064,484 A | 5/2000 | Kobayashi et al. | |
| 7,251,033 B1 | 7/2007 | Phan et al. | |
| 7,873,204 B2 | 1/2011 | Wihl et al. | |
| 9,518,935 B2 | 12/2016 | Guan et al. | |
| 2003/0091224 A1 | 5/2003 | Wiley et al. | |
| 2008/0187842 A1* | 8/2008 | Hung | G03F 1/84 430/5 |

(Continued)

FOREIGN PATENT DOCUMENTS

| | | |
|---|---|---|
| CN | 102084396 A | 6/2011 |
| CN | 102792297 A | 11/2012 |

OTHER PUBLICATIONS

"U.S. Appl. No. 14/278,277, Notice of Allowance dated Oct. 6, 2016", 7 pages.

(Continued)

*Primary Examiner* — Ali Bayat
(74) *Attorney, Agent, or Firm* — Kwan & Olynick LLP

(57) ABSTRACT

Disclosed are methods and systems for inspecting photolithographic reticles. A first and second reticle that were fabricated with a same design are obtained. A first and second reticle image of the first and second reticles are also obtained. The first reticle image is compared to the second reticle image to output a difference image having a plurality of difference events corresponding to candidate defects on either the first or second reticle. An inspection report of the candidate defects is then generated.

28 Claims, 14 Drawing Sheets

(56) References Cited

U.S. PATENT DOCUMENTS

| | | | |
|---|---|---|---|
| 2008/0304056 A1 | 12/2008 | Alles et al. | |
| 2011/0229009 A1* | 9/2011 | Isomura | G01N 21/95607 382/144 |
| 2011/0286658 A1 | 11/2011 | Mitsui | |
| 2013/0111417 A1 | 5/2013 | Hess et al. | |
| 2014/0307254 A1* | 10/2014 | Yamashita | G01N 21/95607 356/237.5 |
| 2015/0029498 A1 | 1/2015 | Guan et al. | |
| 2015/0204796 A1* | 7/2015 | Nagahama | G01N 21/8806 356/237.5 |
| 2015/0221075 A1* | 8/2015 | Watanabe | G06T 7/001 382/144 |
| 2016/0019689 A1* | 1/2016 | Inoue | G06T 7/001 382/149 |
| 2016/0042505 A1* | 2/2016 | Tsuchiya | G06T 7/001 382/144 |
| 2017/0053395 A1 | 2/2017 | Guan et al. | |

OTHER PUBLICATIONS

"U.S. Appl. No. 15/344,788, Notice of Allowance dated Oct. 11, 2017", 8 pgs.

"Chinese Application Serial No. 201480049582.0, Office Action dated Apr. 12, 2017", 9 pgs.

PCT International Search Report for International Application No. PCT/US2018/018578, Filed Feb. 19, 2018, dated Jun. 1, 2018. 3 pages.

* cited by examiner

INSPECTION OF PHOTOMASKS BY COMPARING TWO PHOTOMASKS

TECHNICAL FIELD OF THE INVENTION

The invention generally relates to the field of reticle inspection. More particularly the present invention relates to techniques for qualifying or requalifying reticles in the IC (integrated circuit) fabrication context.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are increasingly smaller. The device needs to be fault free prior to shipment to the end users or customers.

An integrated circuit is typically fabricated from a plurality of reticles (also referred to as "photomasks" or "masks"). Generation of reticles and subsequent inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device or die. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write a plurality of reticles that will later be used to fabricate the particular IC design. For example, an electron beam writer or laser scanner may be used to expose a reticle pattern. A finished reticle or photomask typically has at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is free of defects or degradation, but sometimes has defects that were introduced during fabrication. A reticle inspection system may then be used to inspect the reticle for defects that may have occurred during the production of the reticles. However, the reticle may become defective after use. Thus, there is a continuing need for improved reticle inspection techniques and apparatus.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting photolithographic reticles is disclosed. A first and second reticle that were fabricated with a same design are obtained. A first and second reticle image of the first and second reticles are also obtained. The first reticle image is compared to the second reticle image to output a difference image having a plurality of difference events corresponding to candidate defects on either the first or second reticle. An inspection report of the candidate defects is then generated.

In a specific implementation, the first and second reticle images are obtained in a same inspection tool by loading the first and second reticles together into such inspection tool. In a further aspect, the first and second reticle images are also corrected for focus differences and/or light level differences of same locations on both the first and second reticles prior to comparing such first and second reticle images. In another aspect, the first and second reticle images are obtained in a same inspection tool by successively loading the first and second reticles into such inspection tool one after the other. In an additional aspect, the first and second reticle images are corrected for focus differences and/or light level differences for same locations on both the first and second reticles prior to comparing such first and second reticle images.

In another embodiment, the first and second reticle images are obtained by different inspection tools, and the method further comprises correcting the first and second reticle images for tool parameter differences that affect same locations of the first and second reticle images prior to comparing such first and second reticle images. In another example, comparing the first reticle image to the second reticle image to output a difference image includes (i) for each of a plurality of patches of each of the first and second reticle images, determining an average or mean intensity value for a plurality of locations in each patch, and (ii) comparing each patch's average or mean intensity value from the first reticle image to a corresponding one of the patch's average or mean intensity value at a same location in the second reticle to obtain a plurality of difference average or mean intensity values, which are analyzed to determine whether such difference average or mean intensity values are to be defined as candidate defects. In a further aspect, the difference average or mean intensity values are correlated to critical dimension (CD) variations. In another embodiment, the first and second reticles each include a single die. In another example, comparing the first reticle image to the second reticle image comprises aligning the first and second reticle images to each other to have a maximum matching alignment between such first and second reticle images.

In an alternative embodiment, the method further includes (i) performing a cell-to-cell inspection on the first reticle image prior to comparing the first and second reticle images and (ii) eliminating regions of the first and second reticle images that passed the cell-to-cell inspection from being compared to each other. In another example, the first reticle is newly manufactured and has not been used in a photolithography process, and the second reticle has been used in a photolithography process. In another aspect, the first and second reticles are both new and have not been used in a photolithography process, and the candidate defects found for the first and second reticles when they are new are defined as baseline events. In this aspect, after the baseline events are defined, one or both first and second reticles are used in a photolithography process. The operations for obtaining a first and second reticle image and comparing such first and second images are repeated after the first or second reticle has been used by excluding any resulting difference events that match the baseline events from the inspection report.

In certain embodiments, the invention pertains to a system for inspecting a photolithographic reticle. The system includes at least one memory and at least one processor that are configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

Figure 1A:
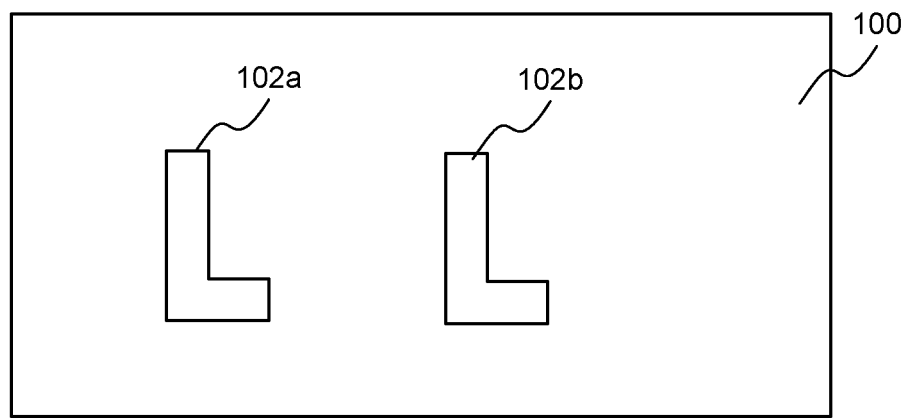
FIG. 1A is a diagrammatic top view of a reticle portion having two pre-OPC features that have a same shape and size.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

A "reticle" generally includes a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, and a chromeless phase lithography PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

There are various ways to inspect reticles for defects that may affect yield in the fabricated devices. Example techniques include die-to-die inspection, cell-to-cell inspection, and die-to-database inspection. In a die-to-die approach, multi-die reticles can be inspected using techniques that compare the images acquired from one die to images acquired from of a second die. A cell-to-cell inspection generally includes comparing images from cell portions of a die that are designed to be identical. A die-to-database approach includes comparing an image obtained from a die to an image that is rendered from a corresponding die as described in the design database.

Although these inspection techniques work well in certain applications, each approach has weaknesses that can lead to inaccurate or inefficiently obtained results. A die-to-die approach would not work for single die reticles. When sections of the patterns are repeated or are simple enough to be self-referencing, reference patterns can be found or synthesized. Comparisons to these found or synthesized references can be used to detect defects. However, suitable references cannot be found or synthesized for all sections of the pattern. For instance, large areas of a typical die contain nonrepeating logic patterns, which cannot be inspected by a cell-to-cell inspection. Additionally, it is often difficult to perform a cell-to-cell inspection since identical cells, even if designed to be identical, are not typically available due to deliberate variations in optical proximity correction (OPC) structures. In general, the terms OPC, SRAF, thin-line, and non-printable structures are used interchangeably herein.

A photolithograhy mask or reticle can include device design data that is generated by circuit and layout designers and/or synthesis tools. Pre-OPC design data generally include polygons that were generated by a designer or synthesis tool for a reticle prior to any OPC structures being added to the design data. The pre-OPC design data can be said to represent the intention of the designer and will generally resemble the final patterns on wafer, which will be fabricated with a reticle that is made using the reticle design data. It is understood that in the multi-patterning cases, the pre-OPC may not represent the final patterns on wafer. FIG. 1A is a diagrammatic top view of a reticle portion 100 having two pre-OPC features 102a and 102b that have a same shape and size.

The reticle design data may include OPC decorations that are added to the pre-OPC reticle design data. In general, OPC software is used to analyze a reticle design and then add OPC decorations to a reticle design based on such analysis. One or more OPC-generating models may be applied to the pre-OPC design so that OPC structures are generated based on such models. The models may be based on experimental and/or simulation results. The OPC decorations are used to enhance the fabrication of the reticle. For example, a sharper image may be obtained on corners if certain OPC enhancements are added proximate to such corners in the design data.

Figure 1B:
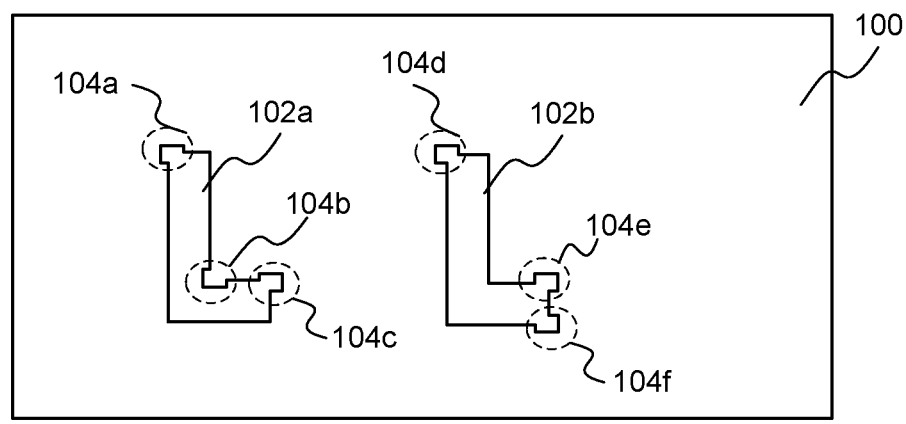
FIG. 1B illustrates the two identical patterns of FIG. 1A with the addition of OPC decorations.

One side-effect of OPC software is a high level of inconsistency of the OPC decorations that are placed with respect to identical design patterns. FIG. 1B illustrates the two identical patterns 102a and 102b of FIG. 1A with the addition of different OPC decorations. As shown, the OPC software adds decorations 104a~c to the first L-shaped pattern 102a, while adding OPC decorations 104d~f to identical L-shaped second pattern 102b. In this example, decorations 104a and 104c of pattern 102a have a same shape and location as the decorations 104d and 104e of pattern 102b. In contrast, second pattern 102b has an additional OPC decoration 104f, while the first pattern 102a has a decoration 104b in the form of removed notch portion 104b in the "crook" of the L shape, while L-shaped pattern 102b remains intact in this same area.

The OPC software for adding OPC decorations may be executed on a same pre-OPC layout and result in different OPC decorations for various reasons. For instance, the type and number of OPC decorations for a given feature may depend on the order such feature is analyzed with respect to other features. Additionally, an edge feature of a feature array may be given a different OPC decoration than an identical center feature in the same array. OPC software may add different OPC decorations to identical features that have different contextual features or background. Even features having a same context may be given different OPC decorations based on grid snap differences between different features. Thus, even identically designed dies may have numerous variable OPC structures that make cell-to-cell inspections produce a high number of false candidate defects.

In another example, a single-die inspection includes algorithms for analyzing the image features of a reticle to identify unusual events, which tend to include different OPC decorations for the underlying design features (e.g., pre-OPC features). For instance, the single-die inspection process may define different decorations (104b of pattern 102a, 104f of pattern 102b) as unusual or candidate events. Since the OPC software tends to result in a high number of variable OPC decorations, a high number of candidate events are typically flagged during a conventional single-die inspection of such a reticle pattern. An event may include any features that are not present in another identical die or die portion that is located a same location in such other identical die, an absence of a feature that is present in another identical die, etc. These OPC-origin candidate events can represent a significant amount of noise for locating "real" printable defects.

Additionally, a reticle may include artifacts (e.g., extra or missing material) that were not intended by the designers to be part of the reticle design pattern. However, certain unintentional artifacts may be determined to not limit the yield of wafers produced with such reticle. The single-die inspection may also identify non-printing or non-yield-limiting unusual events as candidate defects.

Both single-die and multi-die reticles can be inspected using techniques that compare the images acquired from the reticle to images rendered from the post-OPC (optical proximity correction) database. This technique requires access to the post-OPC database and is typically deemed too costly and complex to be practical for requalification of a reticle. After all, the pattern fidelity of the reticle has already been verified by mask shop or incoming quality control inspections. Requalification inspections need only find defects that get added during reticle usage. However, without a second die- or a database-provided reference, finding these defects on a single-die reticle can be challenging.

Certain embodiments of the present invention make use of the fact that more than one copy of a reticle is often manufactured for wafer fabrication. More specifically, two or more identical reticles can provide the opportunity to compare two reticles of identical design to each other. The two reticles can be imaged together or in quick succession, thereby, eliminating tool-to-tool and long-term tool variations. In one embodiment, the reticles are imaged together in the same tool. In another embodiment, each reticle is individually loaded into the same tool and imaged in quick succession. In another embodiment, each reticle is loaded and imaged in different inspection tools. Although the following examples are described with respect to two reticles, more than two reticles may be inspected. Although the following example embodiments are described with respect to a reticle, any suitable type of sample may be monitored using such techniques or systems.

Figure 2:
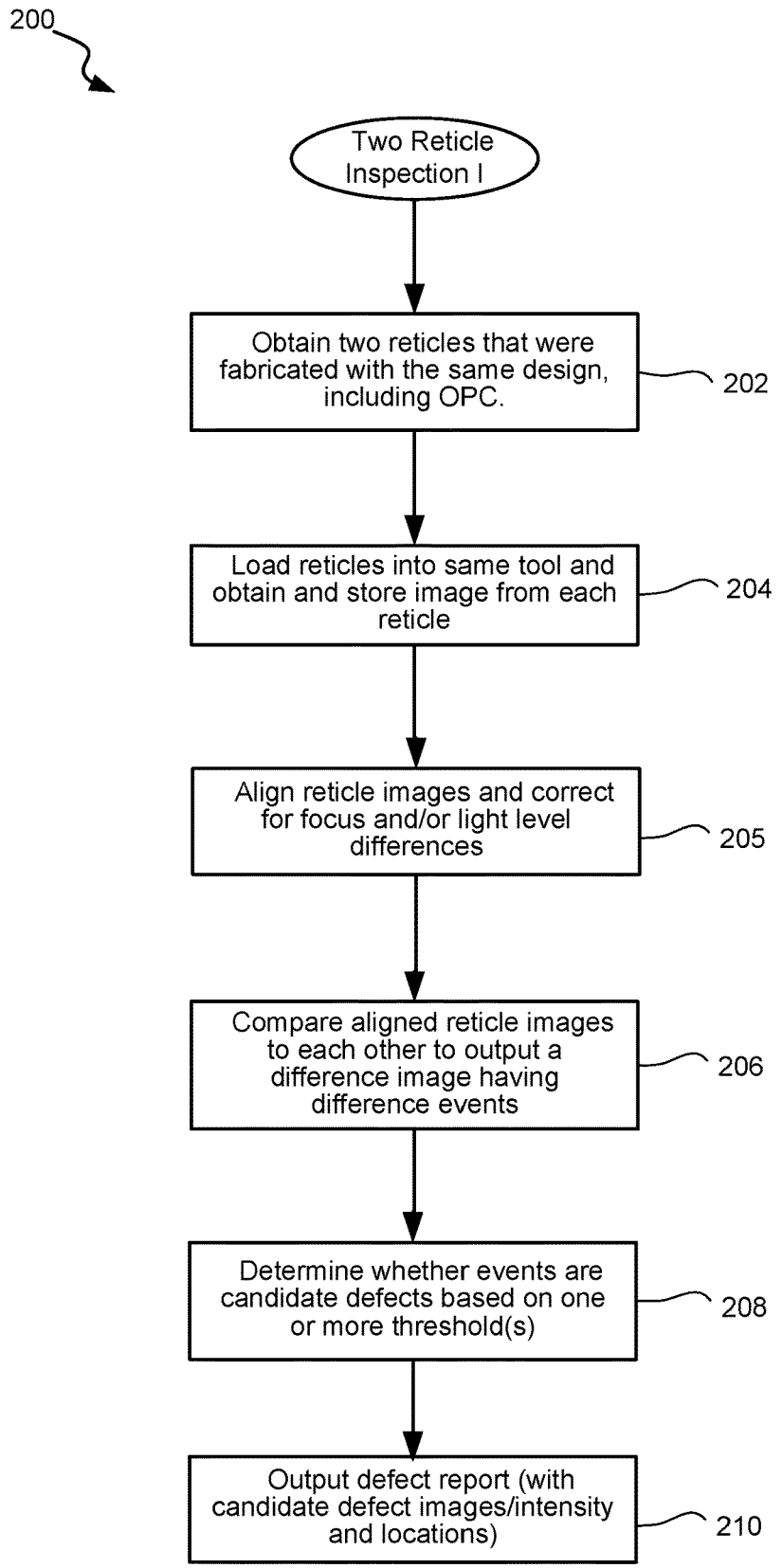
FIG. 2 is a flow chart illustrating a process for inspecting two reticles in a same tool in accordance with one embodiment of the present invention.

FIG. 2 is a flow chart illustrating a process 200 for inspecting two reticles in a same tool in accordance with one embodiment of the present invention. Initially, two reticles that were fabricated with the same design, including OPC structures, may be obtained in operation 202. In general, reticle images for the two reticles may be obtained in any suitable manner. In the illustrated embodiment, the reticles are loaded together into a same inspection tool in operation 204. An image of each reticle may also be obtained and stored in operation 204. In a specific implementation, the stage of the inspection tool is large enough to accommodate two or more reticles. The reticles may then be imaged at the same time by two or more illumination and collection channels. Alternatively, the reticles may each be sequentially imaged by the same illumination and collection channel. For instance, a first reticle on the stage is imaged and then a second reticle on the same stage is immediately imaged after the first reticle.

Regardless of how the reticle images are obtained, the images may then be aligned with each other in operation 205. The images may be aligned in any suitable manner as described further below. Additionally, focus and/or light level differences between the two reticle images may be corrected in operation 205 as described further below.

The aligned reticle images may then be compared to each other to output a difference image having difference events in operation 206. For instance, the image of one reticle image may be subtracted from the image of another reticle to obtain a difference image. For example, the intensity values from each same reticle image pixel can be subtracted. In another example, two intensity averages for the pixels in each pair of reticle image portions that represent multiple pixels are compared or subtracted as further described below. The difference values are all referred to herein as "events".

It may then be determined whether the events are candidate defects based on one or more threshold(s) in operation 208. Any suitable type and number of defect analysis may be performed on the events to detect candidate defects. For instance, desense processing may optionally be performed on each event. In a desensing process, a less stringent (or different) threshold or algorithm may be used to determine whether each event is a defect for one or more predefined areas or feature types of the reticle that have been identified as being less sensitive to false defects/artifacts, as compared to other areas or feature types that are more sensitive to false defects. In one example, a user may have set up a recipe to analyze different reticle areas or types of features (e.g., edges, etc.) in a different manner, such as using different thresholds.

A defect report for the candidate defects may then be output in operation 210. The defect report may be in any suitable format. In one implementation, the defect report may contain a reference to an image and location for each candidate defect. It is noted that each candidate defect corresponds to a difference between the reticle images, which corresponds to a candidate defect image portion or area from one or both reticle images. An image of each candidate defect area may be stored for later review. In another example, the defect report is an image comprised of intensity differences that were defined or flagged as potential defects. The report may be in the form of a defect map having varying colors that correspond to varying intensity or average intensity differences for the candidate defects as further described below.

In another embodiment, the two reticles are sequentially inspected in the same tool one immediately after the other. In some situations, the reticles may not be available at the same time or a tool with a large enough stage to accommodate the two reticles side-by-side is not available. Although not required, the reticles are preferably inspected within about 1 week of each other and, more preferably, within hours of each other. However, the reticles may be inspected within 4 weeks or longer of each other (e.g., even 1 year or longer). It is understood that no preventive maintenance or alteration of operating parameters on the inspection tool shall occur between these two inspections to ensure nearly identical optical conditions.

Figure 3:
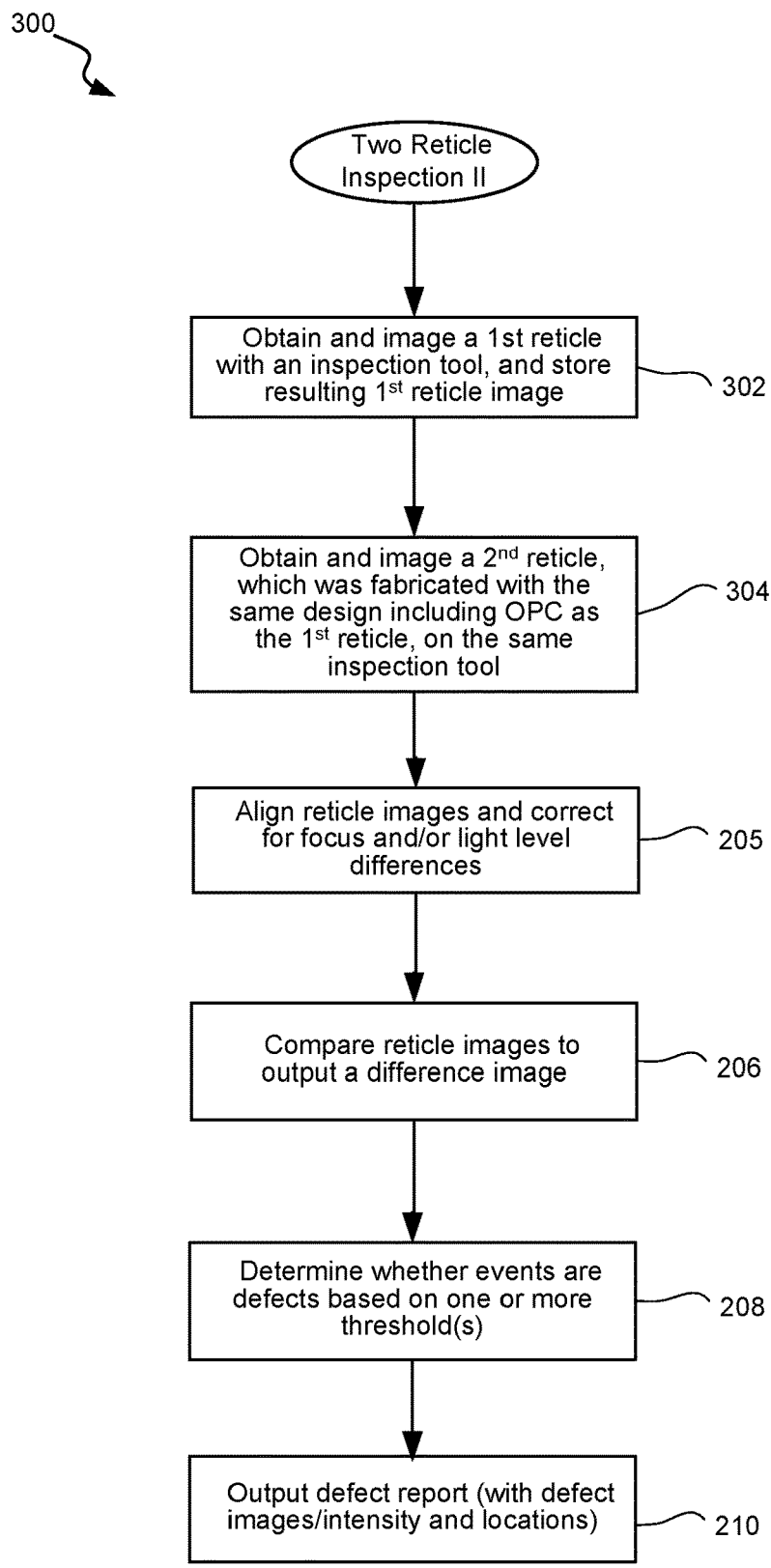
FIG. 3 is a flow chart illustrating an inspection process for detecting defects using two reticles that are successively imaged in the same tool in accordance with an alternative embodiment of the present invention.

FIG. 3 is a flow chart illustrating an inspection process 300 for detecting defects using two reticles that are successively imaged in the same tool in accordance with an alternative embodiment of the present invention. Initially in operation 302, a first reticle is obtained, and such first reticle is imaged with the resulting first reticle image being stored. Next operation 304, a second reticle is obtained, and such second reticle is imaged with the resulting second reticle image being stored. The other operations and the same-labelled operations of FIG. 2 can be performed similarly. However, it is recognized that using the same tool to inspect two reticles at once may require a different amount of correction than sequentially imaging two reticles. Additionally, any suitable correction processes may be utilized for each application as further described herein.

Figure 4:
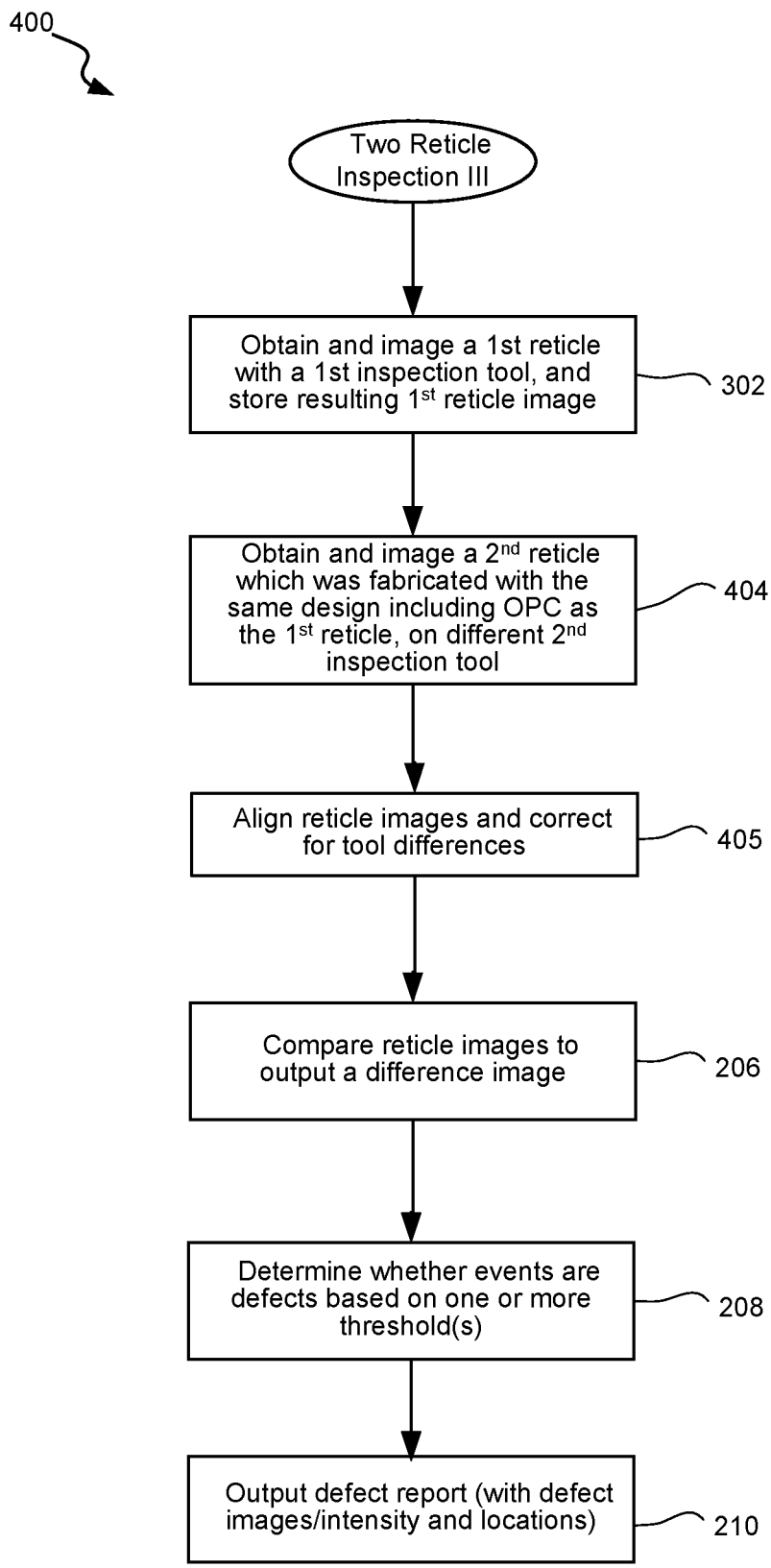
FIG. 4 is a flow chart illustrating an inspection process for detecting defects using two reticles in two different tools in accordance with yet another alternative embodiment of the present invention.

In yet another embodiment, the reticles are inspected and imaged by two different inspection tools. FIG. 4 is a flow chart illustrating an inspection process 400 for detecting defects using two reticles in two different tools in accordance with yet another alternative embodiment of the present invention. The first operation 302 is like the same labelled operation of FIG. 3 in that a first reticle is obtained and imaged with a first tool, and the resulting first reticle image is stored. A second reticle, which was fabricated with the same design including OPC as the first reticle, is also obtained and imaged on a different second tool in operation 404. The images are then aligned and corrected for tool differences in operation 405. Any tool differences (e.g., focus, light level, optical aberrations, etc.) that affect the same locations of the two reticle images may be corrected as described further herein. The other operations are like the same-labelled operations of FIG. 2.

In other embodiments, comparison of intensity values or intensity changes between two reticles may also be correlated to changes in critical dimension (CD). In one implementation, average intensity values for corresponding multiple-pixel areas from two reticles are analyzed. The techniques and systems for inspecting a reticle can be used to detect defects or variations in critical dimension (CD) of reticle features or the like. Although any of the example techniques described herein can also be applied to detecting CD variation or uniformity (CDU), any of these example implementations can also be applied to the monitoring of other sample characteristics, besides CD variation.

In general, the opaque, absorbing, partially opaque, phase-shifting material is formed into pattern structures that are designed and formed with critical dimension (CD) widths, which also results in clear spaces between the structures that also have a CD. A particular CD value may generally affect how a particular reticle feature is transferred to the wafer in the photolithography process and such CD is chosen to optimize this transfer process. Said in another way, if a certain reticle feature's CD value is within a specified CD range, such CD value will result in fabrication of a corresponding wafer feature that allows proper operation of the resulting integrated circuit, as intended by the circuit designer. Features are typically formed with minimum dimensions that also result in operational circuits so as to conserve integrated chip area.

A newly fabricated reticle may include CD (or other film or pattern characteristic) defect issues. For example, the reticle may have defective CD regions, such as mask-writer swath-errors. A reticle may also become damaged over time in a number of different ways. In a first degradation example, the photolithographic exposure process may result in physical degradation of the opaque material of the reticle. For instance, a high power beam, such as a high powered deep ultra violet (UV) beam at 193 nm, that is used on the reticle may physically cause damage to the opaque material on the reticle. Damage may also be caused by other wavelengths, such as a 248 nm UV beam. In effect, the UV beam can physically cause the opaque patterns on the reticle to slump by blasting the corners off of opaque features and causing the features to flatten. As a result, opaque features may have significantly larger CD widths, as compared to original CD widths, while the spacings between such opaque features may have a much smaller CD width, as compared with the original CD width. This type of degradation is referred to as "chrome" degradation since this type of problem typically occurs in chrome type reticles. Other types of CD degradation may be caused by chemical reactions between the reticle features (MoSi) and the exposure light, cleaning processes, contamination, etc. These physical effects can also adversely affect the critical dimensions (CD's) of the reticle over time. As a result of this degradation, the feature CD values may have significantly changed so as to affect wafer yield. For instance, mask feature widths may be significantly larger than the original line width CD.

Figure 5A:
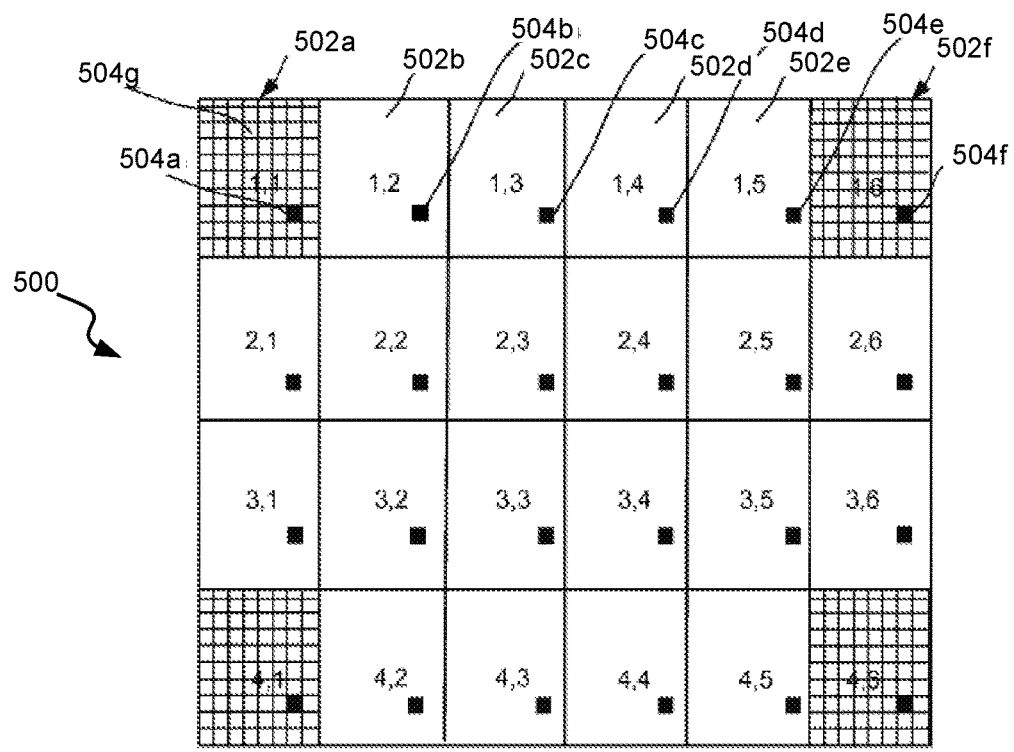
FIG. 5A is a diagrammatic top view of two example reticles having a plurality of identically designed dies for which inspection techniques may be implemented in accordance with another embodiment of the present invention.
Figure 5A:
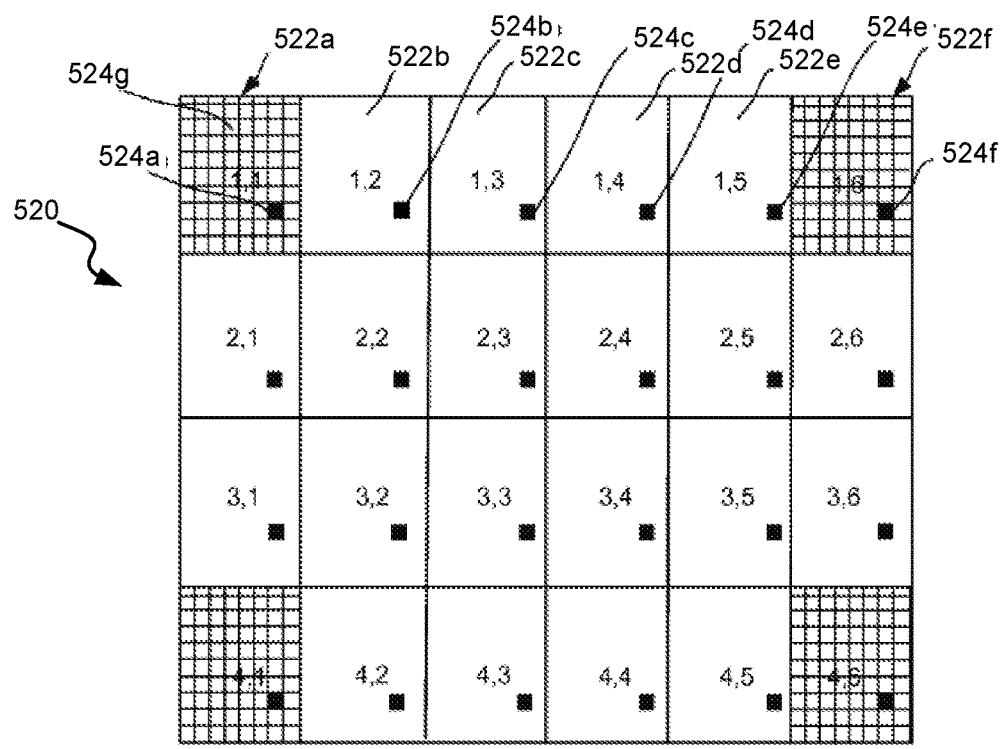

The following average intensity implementations can be used on single die or multiple die reticles. However, a multiple die example is described first. FIG. 5A is a diagrammatic top view of two example reticles 500 and 520 having a plurality of identically designed dies for which inspection techniques may be implemented in accordance with another embodiment of the present invention. As shown, each reticle includes a 6 by 4 array of dies that are designated by row and column. For instance, dies 502a~502f and 522a~522f in the first top row of each of reticle 500 and 520 are designated (1,1), (1,2), (1,3), (1,4), (1,5), and (1,6), from the leftmost column to the rightmost column, respectively. Similarly, the dies of the last row have designations (4,1), (4,2), (4,3), (4,4), (4,5), and (4,6) for each specific row and column.

Although the dies may contain logic patterns as opposed to repeating memory patterns, the dies are designed to be identical to each other. Accordingly, each die portion (referred to as a "patch") of a particular die from either of the two reticles is expected to be identical to at least one other patch from each of the other dies of each of the two reticles. Different patches from different dies in the same or different reticles that are designed to be identical are referred to herein as "die-equivalent." For instance, patch 504b of die 502b of reticle 500 has die-equivalent patches 504a, 504c, 504d, 504e, and 504f in the other dies (e.g., 502a, 502c, 502d, 502e, and 502f) from reticle 500 and die-equivalent patches 524a, 524b, 524c, 524d, 524e, and 524f in the other dies (e.g., 522a, 522c, 522d, 522e, and 522f) from reticle 520.

During inspection, a plurality of patch images of the patches of each reticle, including the dies, may be obtained using an inspection tool. During image acquisition, multiple patch images are obtained for each die. For instance, image patches are obtained for patches 504a and 504g of die 502a. In certain embodiments of the present invention, the image patches are obtained so as to result in die-equivalent patches across the dies of each reticle (or at least one of the reticles), and the die-equivalent patches are processed to detect defects, such as CD defects or CD variation.

In a specific embodiment, the average intensity value for each test patch is compared to an average intensity of the test patch's corresponding die-equivalent patches to obtain a delta map that is related to CD variation across one reticle or between two reticles. The intensity value of each patch may be obtained by averaging reflected and/or transmitted intensity values of the patch's pixels. If the reticle pattern of die-equivalent patches are identical and do not vary in CD (or any other pattern characteristic), the transmitted or reflected light from the die-equivalent patches is expected to be the same. If the reflected or transmitted intensity for a particular patch differs from the other die-equivalent patches, it may be inferred that the pattern of the varying patch has a CD variation as compared to its corresponding die-equivalent patches. For example, an increase in the transmitted intensity infers that the CD of the opaque reticle pattern has decreased and the CD of the clear reticle area has increased.

Figure 5B:
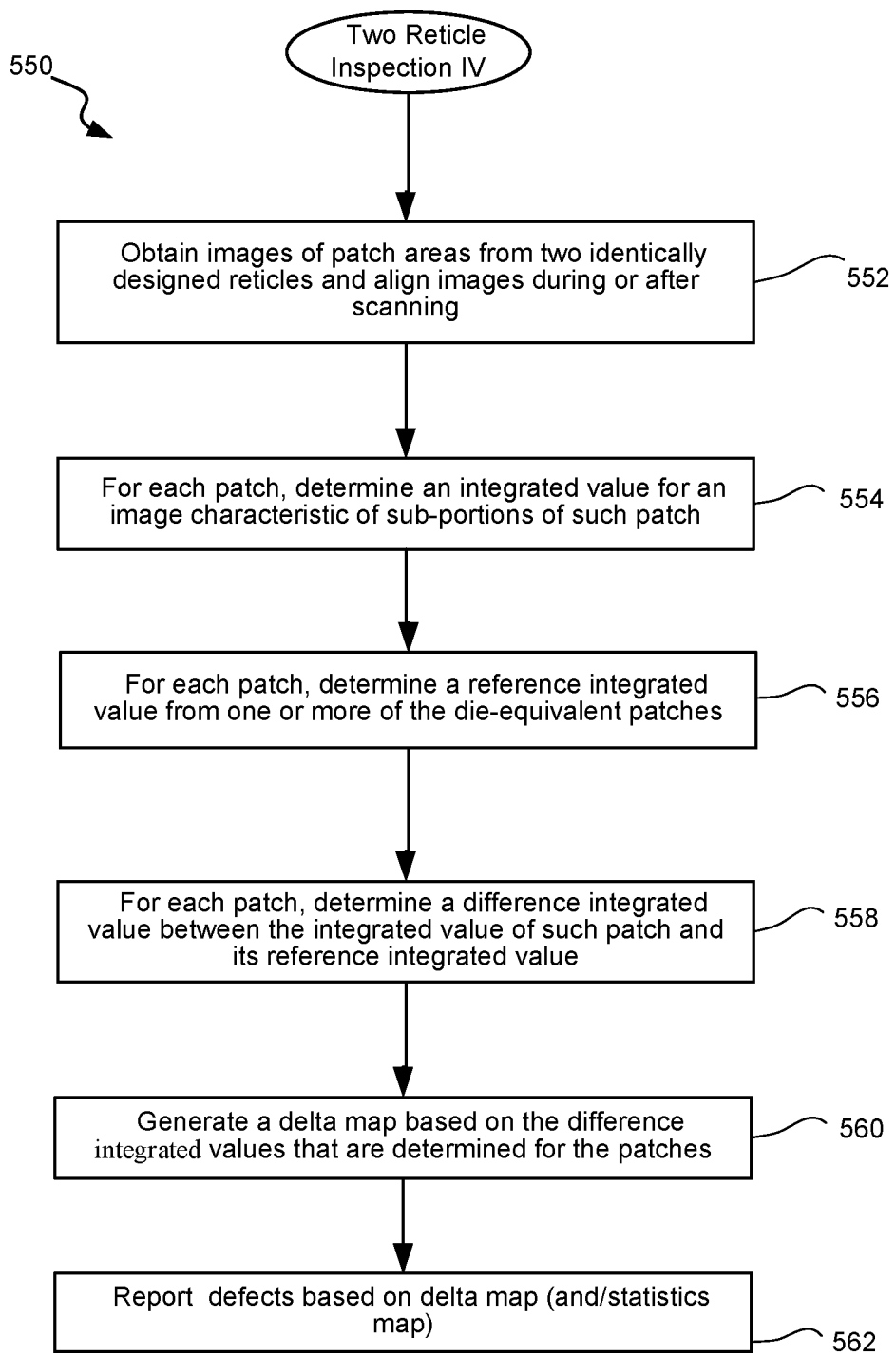
FIG. 5B is a flow chart illustrating an inspection procedure that utilizes die-equivalent patch images in the context of two reticles in accordance with one embodiment of the present invention.

FIG. 5B is a flow chart illustrating an inspection procedure 550 that utilizes die-equivalent patch images in the context of two reticles in accordance with one embodiment of the present invention. The following inspection process 550 may be performed on two newly fabricated reticles so as to detect fabricated defective areas or performed on two reticles that have been used one or more times in a photolithography process so as to detect degradation. Alternatively, this procedure may be used on two reticles with one reticle being newly fabricated and/or unused and the other reticle being used. In this case, the new reticle may be deemed to be defect-free and the used reticle would be deemed defective if a significant amount of CD variation exists between the two reticles. However, it may be possible that the new reticle is deemed defective, instead of the used reticle, after further review of the defects.

In this process, images of die-equivalent patches may be obtained from the reticles in any suitable manner as described further below. For instance, the two reticles can be scanned side-by-side in the same inspection tool so that the die-equivalent patches are aligned during the scan. Alternatively, each reticle may be imaged sequentially in the same tool or in different tools at the same or different times. The example of FIG. 5B illustrates a side-by-side implementation. As shown, images of patch areas of each die of a set of dies from two identically designed reticles are obtained in operation 552. As described further herein, the images may be aligned during or after the images are being obtained.

Figure 6A:
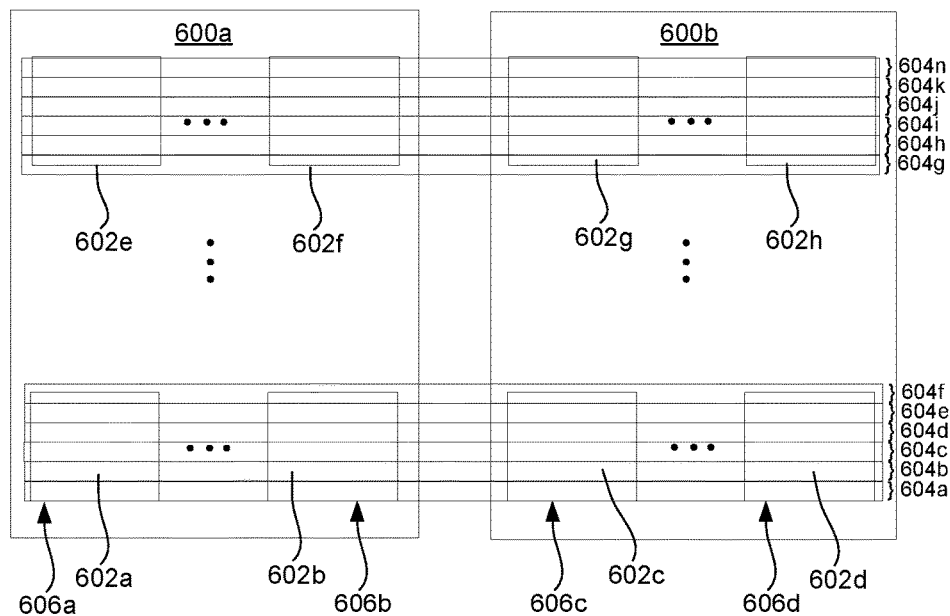
FIG. 6A is a diagrammatic representation of a plurality of scanned/imaged "swaths" of a reticle portion in accordance with embodiment of the present invention.

In a first implementation, each set of die-equivalent patches are obtained from a same scanned swath of patches. FIG. 6A is a diagrammatic representation of a plurality of scanned/imaged "swaths" (e.g., 604a~604n) that go through both a first reticle portion 600a and a second reticle portion 600b in accordance with embodiment of the present invention. That is, each set of die-equivalent intensity data may correspond to a "swath" that goes through both the first reticle portion 600a and the second reticle portion 600b. Each set of die-equivalent intensity data may be obtained by sequentially scanning swaths from the reticles 600a and 600b in a serpentine or raster pattern. For example, the first swath 604a is scanned by an optical beam of an optical inspection system from left to right to obtain a first set of intensity data. The second swath 604b is then scanned from right to left to obtain a second set of intensity data. Swaths are sequentially scanned from the bottom row of dies (e.g.,

602*a*, 602*b*, 602*c*, and 602*d*) of both reticles through the top row of dies (e.g., 602*e*, 602*f*, 602*g*, and 602*h*) of both reticles.

Each scanned swath will contain die-equivalent patches that are each positioned relative to a same reference position in or near its corresponding die for which the swath is obtained. As shown, the swath 604*a* and its patches are positioned with respect to a bottom edge of each patch's respective die (e.g., bottom edges 606*a*~606*d* of dies 602*a*~602*d*, respectively). The bottom edge can be viewed as a reference position for swath 604*a* and its patches.

Figure 6B:
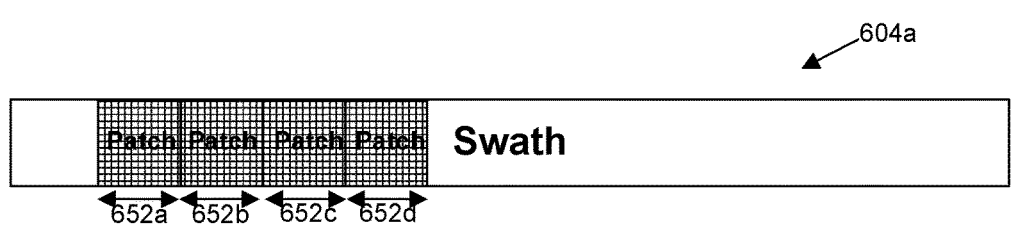
FIG. 6B is a diagrammatic illustration of an intensity data set that corresponds to a reticle swath that is divided into patches in accordance with a specific implementation.

In this first implementation, die-equivalent patches of only a single swath are processed together. FIG. 6B is a diagrammatic illustration of an intensity data set that corresponds to swath 604*a*. The intensity data for swath 604*a* is also divided into a plurality of intensity data sets that correspond to a plurality of patches (e.g., 652*a*, 652*b*, 652*c*, and 652*d*). Intensity data may be collected for multiple points in each patch of each swath.

After the patches from each row or swath are imaged, the image analysis operations of FIG. 5B may be repeated for each imaged set of die-equivalent patches of the scanned swath. Alternatively, the image swaths for the entire reticle may be collected before individually analyzing each row of patches (e.g., each swath's patch images are analyzed together).

In a second implementation, die-equivalent patches of the entire set of scanned swaths for all the dies, which are designed to be identical, are aligned and processed together after the reticle is imaged. Although this second implementation provides improved results over the first implementation for single swath die-equivalent patches as further described below, this second implementation needs to include techniques for carefully positioning the swath scans relative to the dies. One example implementation for aligning die-equivalent swaths is described with respect to FIG. 6C, which illustrates a plurality of scanned swaths that are arranged to have die-equivalent patch images in more than one swath. As shown, the scanned swaths are positioned relative to the dies so that die-equivalent patch images are achieved across multiple swaths. For example, swaths 692*a* and 604*a* include a first set of die-equivalent patch images for dies (e.g., 602*a*~602*h*), while swaths 692*b* and 604*b* include a second set of die-equivalent patch images for dies (e.g., 602*a*~602*h*).

Figure 7:
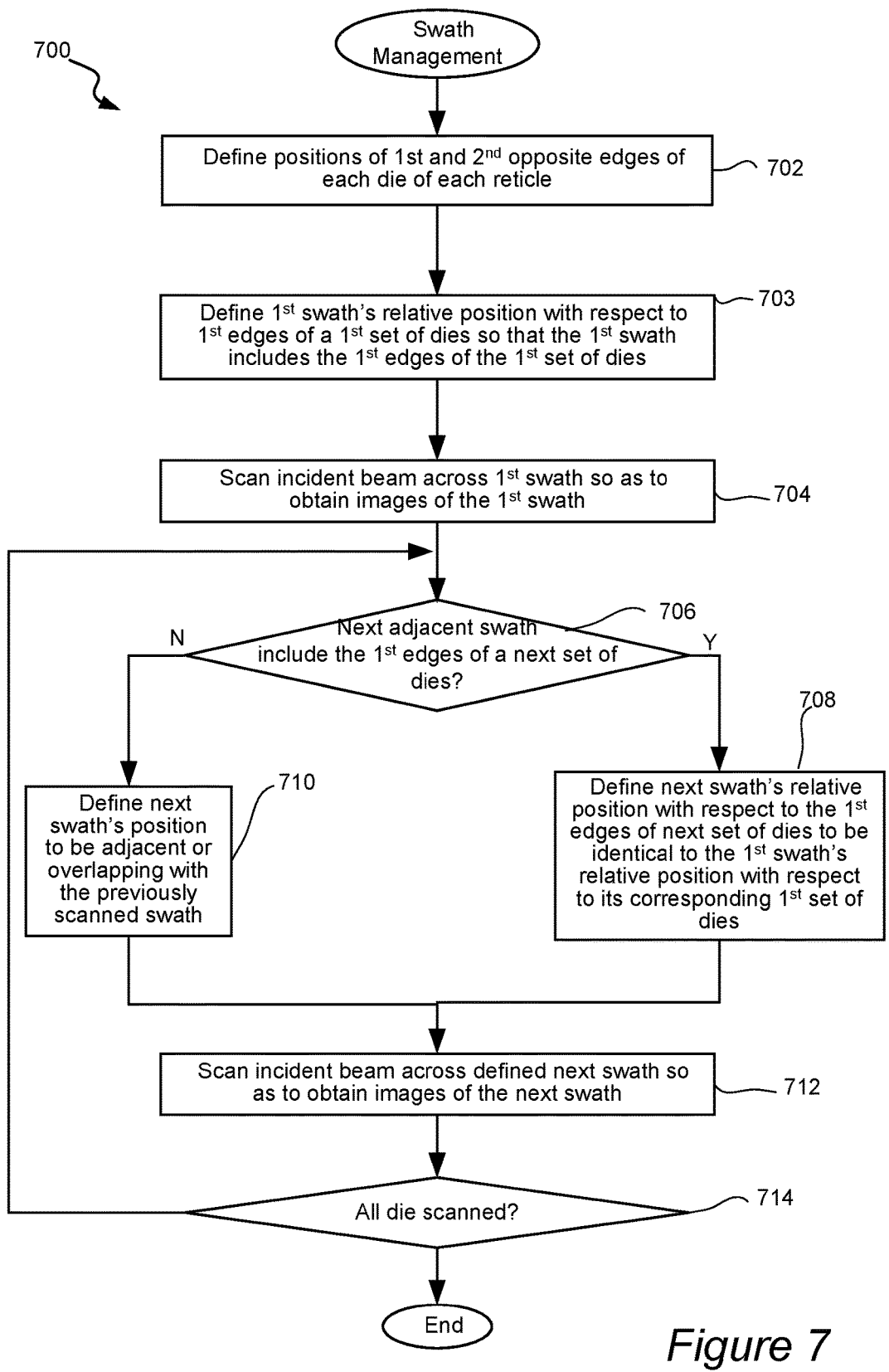
FIG. 7 is a flow chart illustrating a procedure for swath management for achieving die-equivalent patch images across multiple scanned swaths in accordance with a specific implementation of the present invention.

FIG. 7 is a flow chart illustrating a procedure for swath management for achieving die-equivalent patch images across multiple scanned swaths in accordance with a specific implementation of the present invention. In this example, positions of first and second opposite edges of each identical die of each reticle may be defined in operation 702. In general, the inspection tool may be set up with information regarding each die's extent, die offsets, and an array size.

Figure 8:
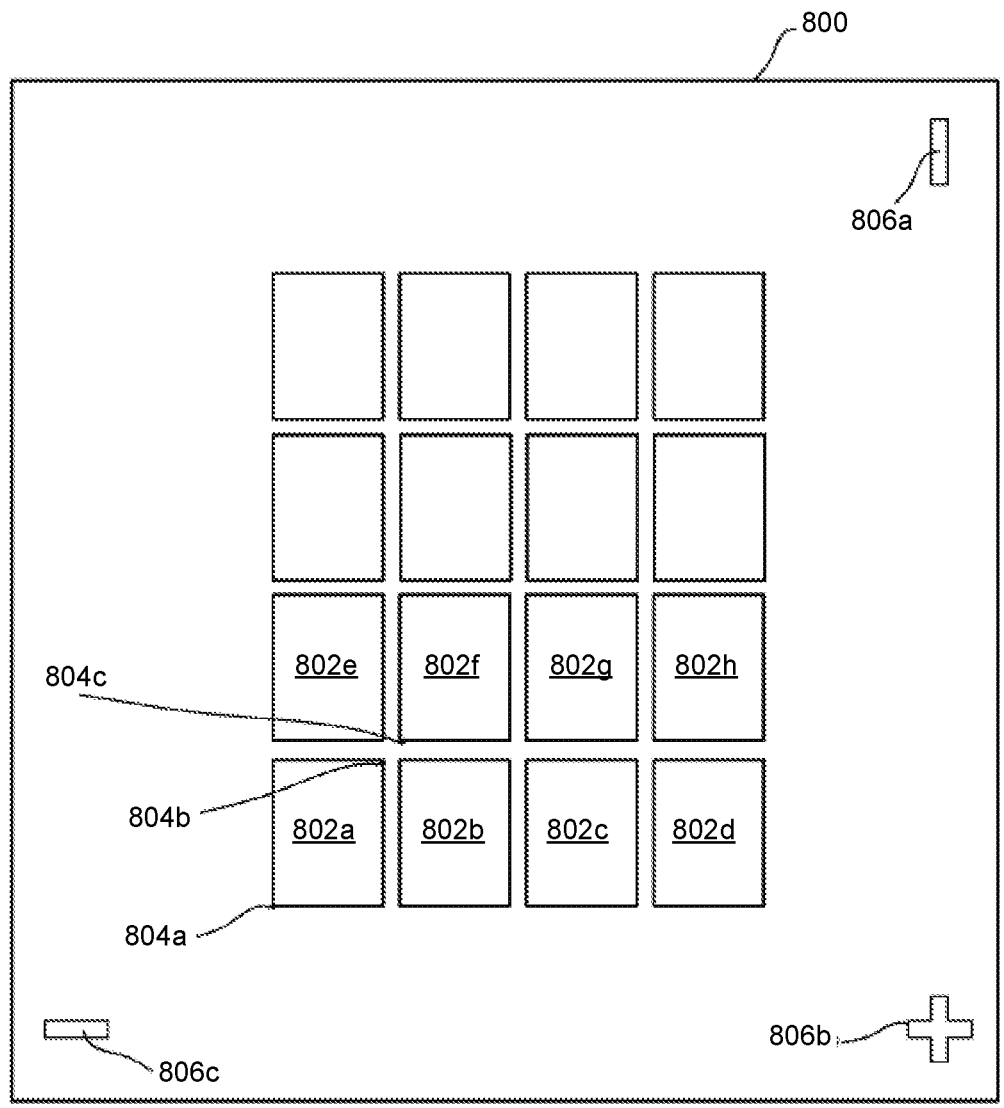
FIG. 8 illustrates a reticle having an array of dies for which an extent, offset, and array size are defined with respect to an inspection tool in accordance with one example implementation of the present invention.

FIG. 8 illustrates a reticle 800 having an array of dies (e.g., 802*a*~*h*) for which an extent, offset, and array size are defined with respect to an inspection tool in accordance with one example implementation of the present invention. In a specific implementation, a setup process for an inspection tool may first include a mechanism for aligning each reticle in the tool. Each reticle may be positioned by a user with respect to any suitable number and type of alignment marks, such as 806*a*~*c*, on each reticle so as to align the reticle and define a particular coordinate system for the scan. Since the alignment marks are printed together with the die patterns on each reticle, the alignment marks will have a same position relative to the dies in each reticle.

Through a setup process for the inspection tool, a user may select points 804*a* and 804*b* to define the extent of a first die 802*a*, as well as all the other dies, in the array of each reticle. In each reticle, the user may also select point 804*c* to define an x and y offset with respect to the first die 802*a* and another die 802*f* to thereby define the offsets between adjacent dies. Other points (not shown) may also be selected to define extents and offsets. The array size may be input by the user into the inspection tool.

Figure 6C:
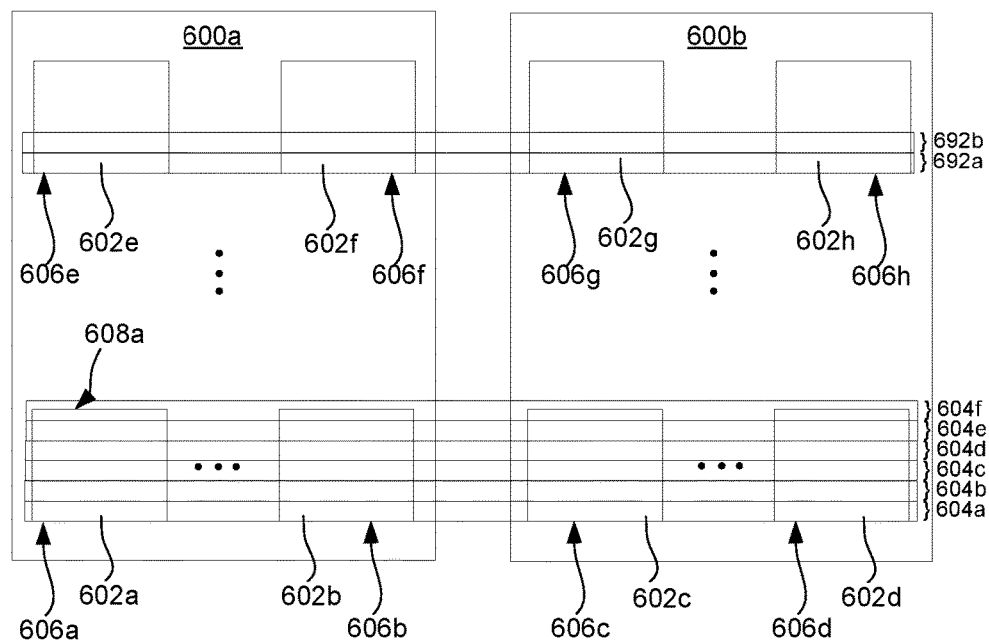
FIG. 6C illustrates a plurality of scanned swaths that are arranged to have die-equivalent patch images in more than one swath in accordance with a second implementation of the present invention.

The inspection tool may use the defined die extent, die offsets, and array size to automatically define each swath position. Referring back to FIG. 7, a first swath's relative position with respect to the first edges of a first set of dies may be defined so that the first swath includes the first edges of the first set of dies in operation 703. In the example of FIG. 6C, the first swath 604*a* is defined relative to the bottom edges (e.g., 606*a*~606*d*) of the first set of dies (e.g., 602*a*~602*d*) from the two reticles 600*a* and 600*b*. The first swath may also be defined relative to any other equivalent positions of the first set of dies. A swath may generally be defined with respect to a particular die position by the inspection tool automatically initiating a scan at a particular swath position.

The incident beam of the inspection tool may then be scanned across the first swath so as to obtain images of a plurality of patches of the first swath in operation 704. In one example, an optical beam may scan across the two reticles and intensity values may be collected for each pixel or point in each patch of the first swath as such beam scans across each patch. Said in another way, the inspection tool may be operable to detect and collect reflected and/or transmitted light from sequentially scanned dies as an incident optical beam scans across each patch of the first swath. Light is collected in response to this incident beam from a plurality of points or subareas of each patch of the first swath.

In the example of FIG. 6C, first swath 604*a* includes a first edge 606*a* of die 602*a*, a first edge 606*b* of die 602*b*, a first edge 606*c* of die 602*c*, and a first edge 606*d* of die 602*d*. Each die also has a second opposite edge (e.g., 608*a*). After the first swath is scanned, it may then be determined whether a next adjacent swath would include the first edges of a second set of dies in operation 706. If the first edge of a second set of dies has not yet been reached, the next swath's position may be defined so that the next swath is adjacent or overlaps with the previously scanned swath in operation 710. The incident beam is also scanned across this defined next swath so as to obtain images of a plurality of patches of the next swath in operation 712. It may then be determined whether all the dies have been scanned in operation 714. If not, next swaths continue to be defined and scanned until all the dies of both reticles are scanned and the scan is complete.

The next adjacent swath that is defined and scanned after the first swath 604*a* in FIG. 6C is swath 604*b*, which has not reached the first edges 606*e*~606*h* of the second set of dies 602*e*~602*h*. In this illustration, the next swath 604*b* is positioned adjacent to the first swath 604*a*. Swaths 604*c*~604*f* are then sequentially defined and scanned as next swaths, which are each positioned adjacent to the previously scanned swath, and these next swaths are sequentially scanned with the inspection tool's beam to obtain patch images.

If swaths would continue to be scanned in a sequential and adjacent swath-to-swath scan pattern, swaths of different rows of dies may have different die portions in each swath as shown in the first implementation of FIG. 6A. For instance, the patch images of the subsequent set of dies (e.g.,

602e~602h) would not be die-equivalent to the first set of dies (e.g., 602a~602d). For example, the patch images of swath 604g are not aligned to the first edges of the second set of dies 602e~602h in the same way that the patch images of the first swath 604a are aligned to the first edges of the first set of dies 602a~602d. This first implementation may work for processing the swaths from dies 602a~602d separately from the swaths from dies 602e~602h.

However, swaths can be obtained and positioned to contain equivalent dies across all the dies of both reticles. To achieve die-equivalent patches across all dies, the illustrated second implementation of FIG. 6C and FIG. 7 includes repositioning of the next scan when it reaches a new set of dies. If the first edges of a second set of dies will be reached in the next scan as explained in operation 708 FIG. 7, the next swath's relative position is defined with respect to the first edges of the second set of the dies to be identical to the first swath's relative position with respect its corresponding set of dies. Each row of dies will have a same first swath that aligns with a same relative die position (e.g., bottom of the dies in the row). In the illustrated example, the first swath to be scanned for dies 602e~602h can be defined as swath 692a (FIG. 6C), which aligns to the first edges 606e~606h of the second set of dies 602e~602h, in the same manner that the first swath aligns with the first edges 606a~606d of the first set of dies 602a~602d. The procedure 700 repeats until the last swath for the last set of dies (e.g., 602e~602h) is scanned.

The swath management process 700 may be used to define die-equivalent patches from all the dies of the two reticles that are being scanned side-by-side. However, if the two reticles are imaged separately, any process may be used to align the resulting two reticle images. For instance, the two reticle images may be overlaid and moved incrementally until a maximum matching alignment is obtained between the two reticle images. Swaths can then be redefined for the two reticles if the swaths are not obtained in an identical manner with respect to alignment with each set of reticle dies, and the die-equivalent patches from the two reticles can be analyzed all together. Alternatively, each pair of reticle patches can be separately analyzed.

Figure 6D:
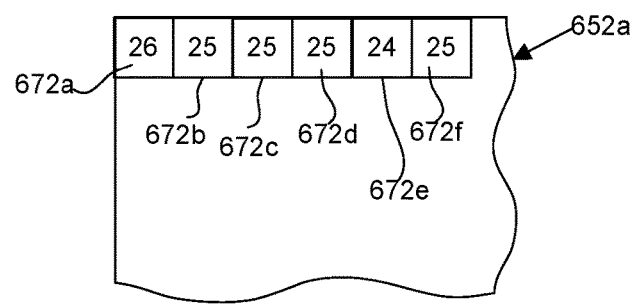
FIG. 6D is a diagrammatic illustration of multiple intensity data sets that corresponds to multiple local areas of each patch of a swath of the reticle in accordance with another implementation.

Regardless of the alignment technique, the patches from both reticles may then be processed as described in FIG. 5B, by way of example. As shown in FIG. 5B, an integrated value for an image characteristic, such as intensity, of sub-portions of each patch (or multiple patches) may be determined in operation 554. FIG. 6D is a diagrammatic illustration of multiple intensity data sets that corresponds to multiple local areas or sub-portions (e.g., 672a~672f) of a patch of a swath of a reticle. In certain implementations, an average or median intensity value may be determined for each patch or set of two or more patches. As shown, multiple intensity values (e.g., 672a, 672b, 672c, 672d, 672e, and 672f) correspond to multiple pixels or points of a particular patch 652a of a particular swath of a reticle. For example, intensity data set 652a corresponding to a patch of the reticle may include intensity values 26, 25, 25, 25, 24, 25, etc. All of the intensity values for each patch (or set of patches) may be averaged together to determine an average intensity value (e.g., 25) for such patch (or set of patches).

The patch portions may be any size and shape, depending on the particular system and application requirements. Although certain embodiments are described with reference to sequentially scanning across rectangular swaths that are aligned perpendicular to the swath scan direction, the reticles may be scanned in any suitable manner. Alternatively, the images may be obtained by scanning the reticles with a different pattern than rastering, such as a circular or spiral pattern, with differently shaped swaths, as long as the swaths are positioned to achieve die-equivalent patch images. Of course, the sensors may have to be arranged differently (e.g., in a circular pattern) and/or the reticles may be moved differently (e.g., rotated) during scanning in order to scan a circular or spiral shape from each reticle.

As a reticle moves past sensors of the inspection tool, light is detected from a rectangular region or "swath" of the reticle and such detected light is converted into multiple intensity values at multiple points in each patch. In this embodiment, the sensors of the scanner are arranged in a rectangular pattern to receive light that is reflected and/or transmitted from the reticle and generate therefrom a set of intensity data that corresponds to a swath of patches of the reticle. In a specific example, each reticle swath can be about 1 million pixels wide and about 1000 to 2000 pixels high, while each patch can be about 2000 pixels wide and 1000 pixels high.

For each patch (or set of patches), a reference integrated value for an image characteristic is determined from one or more of the die-equivalent patches in operation 556. The reference integrated value for each particular patch may be an average of all other die-equivalent patches from both reticles, a sub-portion of the die-equivalent patches from both reticles, or a single die-equivalent patch in the same die location as the test patch's location. For each patch (or set of patches), a difference integrated intensity value between the integrated value of such patch (or set of patches) and its corresponding reference integrated value can then be determined in operation 558. The number of patches for which an average or mean is determined, of course, affects the sampling granularity. That is, a higher number of patches may be used to calculate each average or mean, and a higher number of patches for each calculation is associated with a lower sampling number. However, noise is reduced as more patches are used to determine each average or mean value. In other embodiments, each processor may compare different patch portions of the two reticles.

A delta map may then be generated based on the difference integrated values that are determined for the patch images in operation 560. The delta map will tend to indicate any variation between a pattern characteristic of a particular patch and a reference average or median pattern characteristic of the particular patch's die-equivalent patches from both reticles with optional exclusion of outlier patches.

Embodiments of a delta map can take any suitable form. For example, the delta map can be represented textually as a list of difference or "delta" values for each patch of the reticles. Each delta value may be listed alongside corresponding reticle patch coordinates. The map can optionally or additionally be represented by a metric, such as the standard deviation or variance of the difference integrated intensity values. Alternatively or additionally, a delta map may be represented visually so that different delta values or ranges are shown in different visual ways, such as differently colored reticle patches, different bar graph heights, different graph values, or 3-dimensional representations, etc. The delta values may also be normalized.

When die-equivalent patches from a single swath (or a small number of patches) are processed to form a delta map, "false" echo effects may be generated in non-defective patches from a defective patch. For example, if an intensity value of a defective single patch differs from an average of the other non-defective patches, the defective patch will also cause the average of subsets of the non-defective patch images to increase or decrease by a small amount when each of the non-defective patch images is being assessed with respect to its die-equivalent other non-defective patch images and defective patch image. This small increase or decrease in the reference value affects the difference value for each non-defective patch image. Of course, the defective patch image will have a larger difference with a sign that is opposite the echo effect difference of the other non-defective patch images. Although these echo effects may not be a significant issue when other patch images have relatively large variance, the delta map may contain significant echo-related noise.

One solution to the echo effect, as well as other outlier issues, is to exclude or down weight certain outlier integrated intensity values of the die-equivalent patches when determining the reference value of the die-equivalent patches. Any suitable technique may be used to exclude or down weight outlier values from each reference value calculation. In a specific example, the median value (instead of the average value) of the other die-equivalent patches is used as the reference value. The median will be less influenced by outlier values from one or more defective region and will, therefore, have less corruption of the reference value by one or more defective regions than an average value.

Similarly, integrated intensity values of outlier patch images may be automatically excluded from the calculation for determining each reference value. One way may include eliminating integrated intensity values from the reference value calculation of each patch that has a value that exceeds a predefined threshold. In another example, integrated intensity values that are more than a predefined number of standard deviations from the average of the die-equivalent values may be excluded from each reference value determination. In one example, any integrated value has more than 5 sigma standard deviations may be excluded from a reference value calculation. In other embodiments, 3 sigma or 4 sigma intensity values may be excluded from the reference value determination.

The echo effect may be reduced and scaled down in relation to 1/N, where N is the number of dies used to determine each reference value. In some implementations, the echo effect can be significantly reduced by using all the other dies on both reticles, instead of a single row or swath of dies, to obtain a reference value so that more dies are averaged together. Even when all the other dies on the reticles are used to determine a reference value, reticles that have a low number of dies will to have a smaller echo effect than reticles that have a high number of dies.

In general, intensity values for different regions (such as the pixels of a patch) corresponding to the reflected light may also be combined with the intensity values for the transmitted light before or after determining the average intensity value for each patch. For instance, an average of the reflected and transmitted intensity values may be determined for each point or pixel. Alternatively, the averages may be calculated separately for the reflected and transmitted intensity values of a patch. The separately calculated reflected average and transmitted average for each patch may also be combined or averaged together. In one example implementation, the reflected (R) and transmitted (T) values different regions may be combined by (T−R)/2.

Reflected light generally responds differently to noise sources than transmitted light. For example, a surface roughness affects the reflected light and not the transmitted light. In general, transmitted and reflected light modes both contain the CD signal but have different (uncorrelated) noise sources. Thus, the two modes can be combined to potentially achieve a higher signal-to-noise ratio than either mode would achieve individually. In some cases, R and T signals for particular regions may have a same sign, instead of an opposite sign, which may indicate that the results are inconsistent in the associated regions and may not be trustworthy. Thus, the combination of R and T could be down-weighted in such regions or removed from the computation if insufficiently trustworthy.

In other embodiments, a reflected delta map may be generated using reflected intensity values, and a transmitted delta map may be generated using transmitted intensity values. In a specific technique, the reflected and transmitted delta maps are averaged together to form a combined reflected and transmitted delta map. For instance, the reflected difference value (R) and transmitted difference value (T) of each patch may be averaged together. Since the R and T delta values have an opposite sign, the averaging is performed by the equation (T−R)/2 so that the R and T delta values do not cancel each other out. That is, subtracting the two maps effectively adds the signals together.

Since the noise sources are different for T and R, the noise can tend to be averaged out of the combined signal. In other embodiments, certain noise sources may have a much larger effect on one of the R or T delta maps. For instance, when a haze is formed over the reticle over time, the R delta map will be significantly affected, while the T delta map is not. Thus, if the R and T delta maps were simply averaged together, the intensity changes caused by the haze would not be factored out of the combined delta map. In another technique, the reflected delta values can be weighted differently than the transmitted delta values based on any suitable noise indicator, such as how much the patch's intensity value varies from the average of the die-equivalent patches. In a specific implementation, the combined delta map can be formed using an inverse variance weighting. The following equation may be used to determine a combined reflected and transmitted delta map:

$$(1/(\sigma_T^2+\sigma_R^2))(\sigma_T^2 \Delta I_R/I_R - \sigma_R^2 \Delta I_T/I_T)$$

$\Delta I_R/I_R$ is the reflected delta value expressed as a percentage change; $\Delta I_T/I_T$ is the transmitted delta value expressed as a percentage change; and $\sigma_R$ and $\sigma_T$ are standard deviations from the die-equivalent patches' average reflected and transmitted intensity, respectively.

Other combinations of reflected and transmitted integrated values with weighting that is based on one or more noise factors (fill factor, light calibration, etc.) may be used. The noise factors may be weighted separately or combined. Fill factor corresponds to pattern density. The pattern edges affect the signal so that if there are a lot of edges, the R or T signal may be stronger and visa versa. Likewise, the R or T signal may be affected differently based on light calibration levels.

Defects may then be reported based on the delta map or a statistics map in operation 562. For instance, it may be determined whether any difference intensity value or delta value is above a predefined threshold. Instead of using an absolute threshold to detect CD defects, the threshold can be based on the amount of variance from the average. For instance, delta values that deviate by more than a certain percentage from the average are defined as defects. For instance, a delta intensity of 1 grayscale may be defined as a defect if the corresponding die-equivalent patches' intensity mean is 100 grayscales. Delta intensity values that vary more than a certain number of standard deviations may also be defined as defects.

Figure 9:
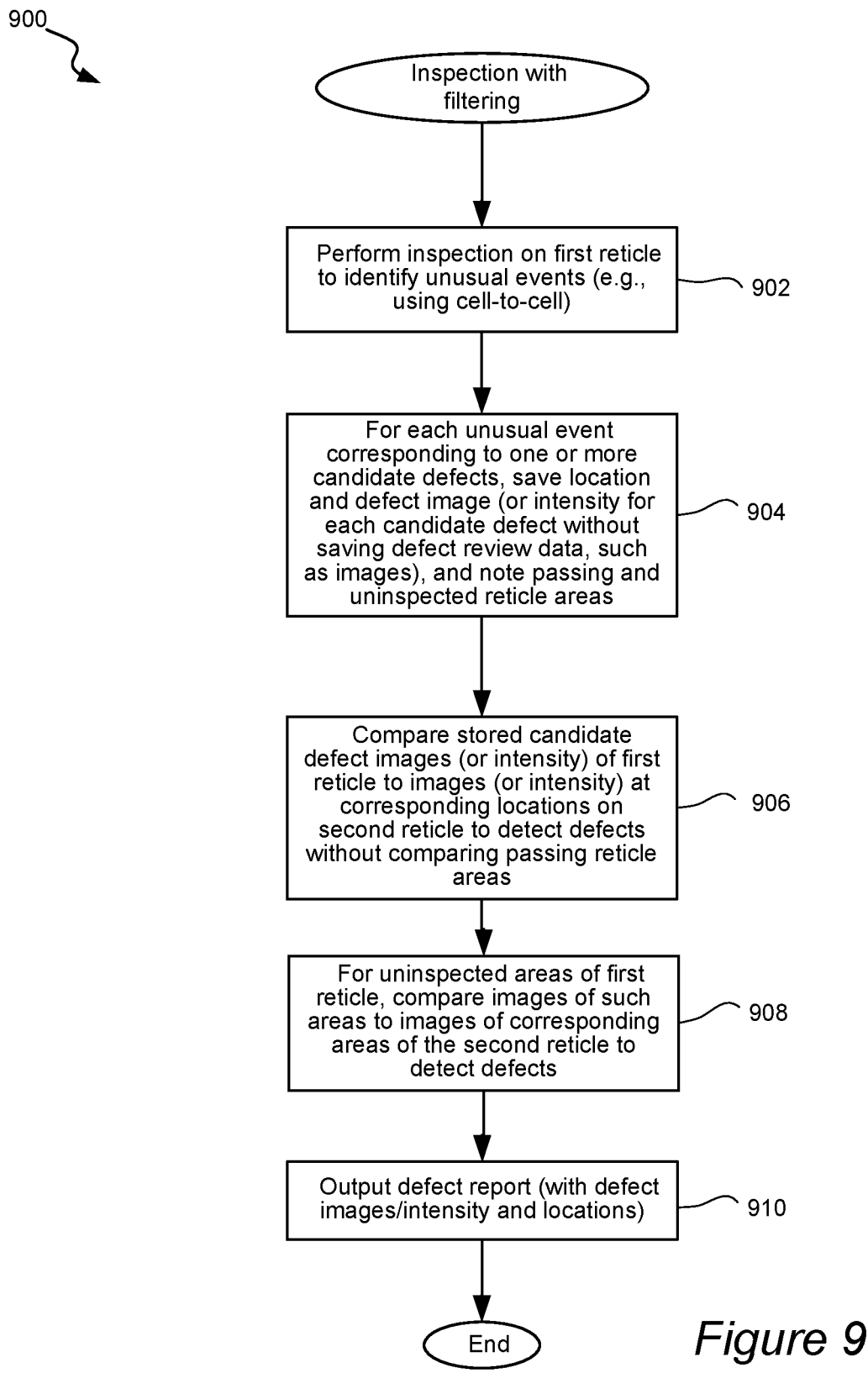
FIG. 9 is a flowchart illustrating an inspection process with filtering in accordance with another embodiment of the present invention.

One or more additional ways for improving inspection efficiency may be implemented in conjunction with any of the inventive techniques described herein. For instance, a cell-to-cell inspection of a first reticle can be used to filter areas of a second reticle from requiring inspection. FIG. 9 is a flowchart illustrating an inspection process with filtering in accordance with another embodiment of the present invention. Initially, an inspection may be performed on a first reticle to identify unusual events in operation 902. In one simple example, a cell-to-cell inspection is implemented on the first reticle. That is, image portions in each die that are designed to be identical are compared with each other to find differences. In another example in which the reticle contains multiple dies, the dies of the first reticle are compared with each other.

Another type of inspection is a single-die inspection that includes implementing a statistical analysis on the image features of a die to locate unusual events, which each may correspond to one or more "candidate events or defects." A single-die inspection process may include any suitable operations for processing image features to identify candidate events. For instance, any suitable combination of image processing techniques can be used to analyze the image features and determine which features are atypical, given the context of such features. In one simple example, if an array of mostly identical bars includes a single bar with a notch formed on the side, the notch may be deemed a candidate defect.

One approach for locating unusual events and candidate defects is described further in U.S. Pat. No. 9,518,935 issued 13 Dec. 2016 by Chun Guan et al., which is incorporated herein by reference in its entirety. Some example single-die approaches include template matching and principal component analysis. Template matching is an image processing technique for using common template features as references to locate unusual features. For instance, a first image feature is grabbed and compared or matched to other features. The first image feature is defined as an unusual or candidate event if there is not another feature (or an insignificant number of features) that matches the first image feature. An exhaustive template matching approach can be used to grab and compare each image feature to the other features. Alternatively, other processes can also be implemented to more intelligently and efficiently locate unusual features. For instance, a set of common feature templates can be initially defined before the reticle images are analyzed. The template image features can be transformed into a feature vector for comparison to other feature vectors. Additionally, certain features can be defined as unusual events even if there are multiple similar events. For example, small features that appear in an otherwise 0D or 1D pattern may be identified as unusual events.

For each identified unusual event corresponding to one or more candidate defects, the location and candidate defect image may be saved, as well as noting passing and uninspected reticle areas, in operation 904. In an alternative embodiment, a location and intensity value for each candidate defect can be saved without saving defect review data, such as the images. The stored location and image/intensity defect data may be referred to as "baseline event data." The baseline event data may pertain to deliberate unusual events, such as unusual events cause by OPC decoration variation for substantially identical design patterns. That is, at least some of the baseline events will general correspond to reticle features, which were designed to be identical prior to an optical proximity correction process (OPC) being implemented on such reticle features to add OPC decorations so that such reticle features are no longer identical. Such baseline event data may also pertain to unintentional or insignificant events that are deemed to not be real defects or cause yield problems.

In the implementation in which only intensity, and not image data, is saved for each unusual event, baseline event data contains a minimal set of data for identifying the same events in a subsequent inspection of the first reticle later (e.g., after use of such first reticle) or a second reticle that is designed to be identical to the first reticle. In the subsequent inspection example, this type of inspection is referred to as a "delta time" inspection. Several embodiments of a delta-time approach are further described in U.S. application Ser. No. 13/757,103, filed 1 Feb. 2013 by Carl E. Hess et al., which application is incorporated herein by reference. In the intensity event data embodiment, the baseline event data for each candidate defect includes a location, such as x and y coordinates with respect to an origin position on the reticle. An origin position on the reticle may be identified in any suitable manner, such as by one or more origin X and/or Y markings on the reticle. For example, a cross-shaped marking may allow the inspection tool to reference the location of each reticle XY position with respect to the center portion of such marking. Other identifying baseline event data may include an intensity value, as well as on which channel the event data's intensity value was obtained (e.g., transmission or reflecting channel).

One or more candidate defects may be found for each unusual event by first finding a reference for each unusual event. Candidate defects may also be referred to herein as unusual events. Each unique region may be dilated all around by a margin amount. A custom sized rectangular clip or template may then be collected from the original image. This clip contains the original image pixels that correspond to the pixels within the dilated unique region.

A 2D array of weights may be set to be the same size as the rectangular clip. These weights may be used to drive a weighted normalized cross correlation search for a reference region. The weights may be set low where the probability of finding matching pattern is low. The weights can increase as the probability of finding matching pattern increases. Since there is something unique near the centers of the unique clips that make up the unique region, the probability of finding matching pattern near these template centers is low. The probability of finding matching patterns increases with distance from these centers and is highest in the non-unique margins that were added. The weights may be set to follow these trends. The weights may be further adjusted so that edges within the pattern are emphasized over flat areas. The weights for any pixels outside the margins but inside the bounding rectangle may be set to zero.

With the weights set, the reticle image may be searched for a patch of the same size that maximizes the weighted NCC (normalized cross correlation) score. When an on-grid patch produces a peak in the weighted NCC score, interpolation may be used to find the fine alignment that maximizes this score. After searching the reticle image, the aligned patch with the highest score may be selected as the reference. If the best-weighted NCC score fails to exceed a minimum threshold, then no suitable reference is found.

For regions that are primarily 0D or 1D, references can be synthesized, instead of found in the reticle image. If an entire region could have been labeled 0D, except for the weak (and strong) axis gradients near the region's center, a 0D reference can be synthesized. All pixels within the synthetic reference may be set to the mean of the test region's margin pixels. This technique can build a purely 0D reference that best fits the test region's margin pixels. If an entire region could have been labeled 1D except for the weak axis gradients near the unusual test region's centers, a 1D reference can be synthesized. For horizontal patterns, each row of pixels in the synthetic reference can be set to the mean of the test region's margin pixels for that row. For vertical patterns, each column of pixels in the synthetic reference can be set to the mean of the test region's margin pixels for that column. For diagonal patterns, the concept can be the same (e.g., build a purely 1D synthetic reference that best fits the test region's margin pixels).

If no reference is found or synthesizable, the particular unusual region can be labeled as uninspected and no further processing is done on that region. If a reference is found, the reference clip is collected and compensated. The collection may use interpolation to incorporate the fine alignment offset. The compensation may use a weighted fitting function to compute correction terms. Lighter weights may be used in the uncertain areas of the region to relax the fit in those areas. Once the corrections are computed they are applied to the reference clip.

Each unusual event's test image may be compared to a corresponding reference image (if found) to determine a difference value. If the difference value is above a predetermined threshold, such difference (e.g., each peak) may be identified as a candidate defect.

For each unusual event for which a reference image cannot be found, the unusual event's image may be stored as a reference image for a subsequent requalification inspection on the same area. Such an event may be deemed uninspectable.

Referring to FIG. 9, the stored candidate defect images (or intensity) of the first reticle may be compared to images (or intensity values) at corresponding locations on a second reticle in operation 906. The second reticle is designed to be identical to the first reticle. The two-reticle comparison results in detection of candidate defects without comparing passing reticles areas of the first reticle to corresponding areas of the second reticle. For instance, an image comparison is not performed for matching cell-to-cell areas of the first reticle to the second reticle or visa versa.

For uninspected areas of the first reticle, images (or intensity values) of such areas may also be compared to images (or intensity values) of corresponding areas of the second reticle to detect candidate defects in operation 908. These uninspected areas do not have a corresponding identical area that can be used for a cell-to-cell inspection. For each image portion (or intensity value) from two corresponding locations of the two reticles, any suitable comparison analysis for finding candidate defects may be performed. For instance, desense processing may optionally be performed on each unmatching image/intensity pair to determine whether a candidate defect has been found. For example, a less stringent (or different) threshold or algorithm, as compared with the threshold or algorithm that was used to identify the event as an unusual event, may be used to determine whether the current event is a candidate defect for particular predefined areas or feature types of the reticle that have been identified as being less sensitive to unusual events/artifacts. That is, a user may have set up a recipe to analyze different types of features (e.g., edges, etc.) in a different manner.

A defect report may then be output in operation 910. This defect report may include defect images or intensity values and their locations, and such data may then be used to more carefully inspect such defect locations, for example, with a high resolution imaging tool. Alternatively, the defect data may simply be written to the inspection report without further defect analysis.

The inspection report may contain any suitable defect review data. For instance, the defect review data may include both reflective (R) and transmission (T) channel images, a difference image between the R and T images, reference R and T images (generated from the single-die process), thumbnail images, intermediate computations to find candidate defects, etc.

In contrast, if a baseline event from the first reticle has a matching event in the second reticle (or visa versa), further defect analysis may be skipped. Additionally, the event's review data is not written to the inspection report. Since defect review data, including numerous images, are not saved as an entry in an inspection report, the inspection report is not likely to reach data size limits. In some inspections, the data pipeline for all the unusual events prior to filtering such events can be 100 times larger than the defect review data that is eventually saved for the inspection report. Data savings for the inspection report, which excludes events that are similar to baseline events, can be significant.

A baseline event and a corresponding event from the second reticle may be determined to match if their locations are at a same location relative to the reticle origin or within a predetermined distance of each other, such as within 0.5 um distance of each other (relative to their die position) and the events have a similar size if the size values are equal or within a 30% of each other. Otherwise, the event is deemed a new event and kept for the inspection report.

Regardless of the inspection approach for two reticles, each set of reticle images are generally adjusted to minimize the differences in the reticle images caused by differences in the inspection tool's operation and effect on the differences between the resulting images. In a specific example, the image differences caused by focus differences are minimized. For instance, a line-space-line feature may result in an image having a waveform with a peak at the line positions and a minimum at the space position. If one image is out-of-focus, the top and bottom of this waveform may appear flattened out. In this case, the in-focus waveform may be flattened out to match the out-of-focus waveform. Model-based focus compensation methods can also be applied by utilizing the transmitted and reflected images simultaneously.

In another example, the inspection light levels are properly calibrated and compensated across each reticle. Two masks may have different R properties (while T may stay the same). For instance, two reticle blanks can be from different batches and experience different fabrication processes. If different process tool, one can also see different T or R values through the same areas of the reticles. If different inspection tools are used to inspect the different reticles, the two reticle images are also adjusted to account for aberration differences between the tools. One such method is to start with a recovered mask pattern that includes the impact of the tool aberrations, and then iteratively derive a mask pattern free of such impact by minimizing the error between predicted T (transmitted) image generated from such aberration-free mask pattern and the measured T image. Several techniques for recovering the mask pattern are described further in U.S. Pat. No. 7,873,204 by Mark J. Wihl et al., which is incorporated herein by reference in its entirety.

Certain embodiments of the present invention efficiently utilize two reticles with the same design. Two different reticles that were made to be identical will not typically have the same defect unless programmed into the design. Thus, defects that are located on one reticle and not the other reticle can be efficiently located by comparison of reticle images (or intensity values). These techniques can also be used on single die reticles. Additionally, the inspection can be performed without use of the design database, which tends to be expensive in terms of time, costs, and modeling challenges. For instance, an inspection tool that is operable to perform a database inspection can be significantly more expensive than a tool that uses a comparison type inspection.

Figure 10:
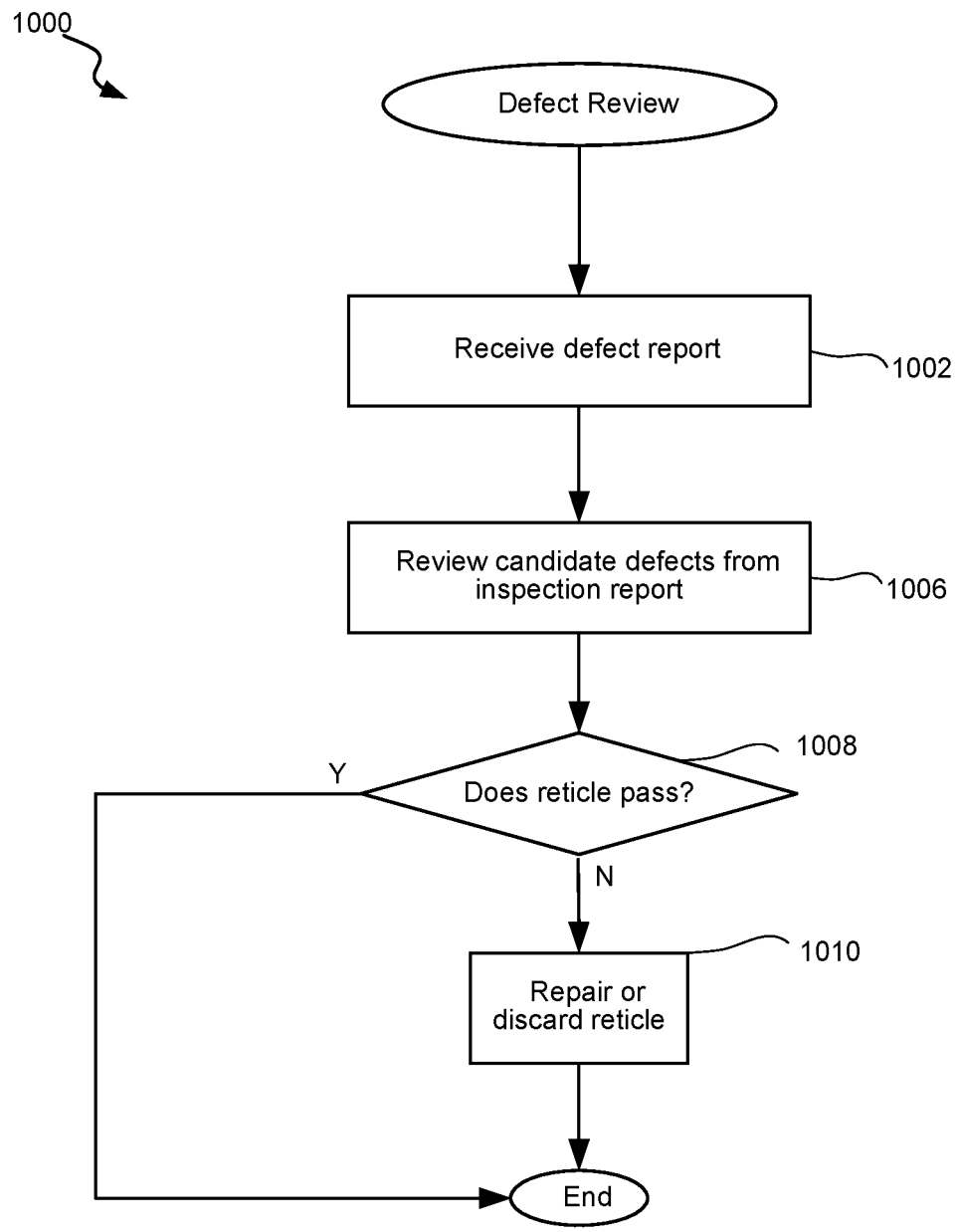
FIG. 10 illustrates an overview of an inspection and defect review procedure 1000 in accordance with one embodiment.

FIG. 10 illustrates an overview of an inspection and defect review procedure 1000 in accordance with one embodiment. As shown, a defect report is received in operation 1002. For instance, any of the inspection processes described herein may be implemented to generate a list of candidate defect events from the two reticles. The defect report for each reticle may be analyzed separately or together.

The candidate defects and their review data from the inspection report may then be reviewed in operation 1006. For instance, an operator may review the images of each defect to determine whether each defect corresponds to a significant or real defect, which limits yield. Additionally, the remaining defects may be analyzed by a classifier tool that classifies the defects into classes so that a subset of each class may be efficiently reviewed by an operator, as opposed to reviewing all the candidate defects.

It may then be determined whether the reticle passes inspection based on such map in operation 1008. For instance, it may be determined whether the image (or intensity) difference is above a predefined threshold. If the size of the image difference or intensity value difference is above the predefined threshold, the corresponding reticle portion may then be more carefully reviewed to determine whether the reticle is defective and can no longer be used.

If a delta-intensity map was generated, it may be determined whether the reticle passes inspection based on such map. If an intensity variation is above the predefined or statistics-based threshold, the corresponding patch may then be more carefully reviewed to determine whether the reticle is defective and can no longer be used. For instance, a SEM may be used to review the defective area to determine whether critical dimensions (CD's) are out of specification. This review process may be implemented on any of the reported candidate defects.

In alternative implementations, specific intensity changes in the delta intensity map can be associated with specific CD variations, which can then be determined to be in or out of specification. For instance, a 1% intensity variation may correlate to a 1% CD variation. Particular intensity changes may be associated with specific CD changes through calibration reticles having pattern areas with multiple known CD values that can be measured to determine intensity differences between different CD changes. An out-of-specification CD variation would result in the reticle not passing the inspection.

Regardless of the inspection approach that is implemented, if the reticle does not pass review, the corresponding reticle can either be repaired or discarded in operation 1010 and inspection ends. For instance, certain defects can be cleaned from the reticle. The photolithography process may also be adjusted based on the delta map. In one implementation, the delta value, $\Delta I/I$, is related to the fractional dose correction, $\Delta D/D$, by $\Delta I/I=-\Delta D/D$. Dose correction based on intensity variation may be determined by the DoseMapper™ methodology available from ASML of Veldhoven, the Netherlands or the CDC correction methodology available from Zeiss of Germany.

If the reticle passes, the review process may end without discarding or repairing the reticles. The passing reticles may be used to fabricate wafers. After a reticle (repaired or passing reticle) is again used, the reticle may again be inspected by comparing to its corresponding other reticle that was designed to be identical to the first reticle.

In an alternative embodiment, if the reticles pass inspection, all the candidate defects can be deemed "acceptable differences", and such acceptable difference values can be stored and later reused to quickly requalify either or both reticles after such reticles have been used. In this example, the "acceptable differences" are used as a set of baseline events. If such baseline events are present on a used reticle, such baseline events can be deemed acceptable and not reported as candidate defects. Only differences that have occurred since the baseline events were detected are determined to be candidate defects and subject to defect review.

Figure 11:
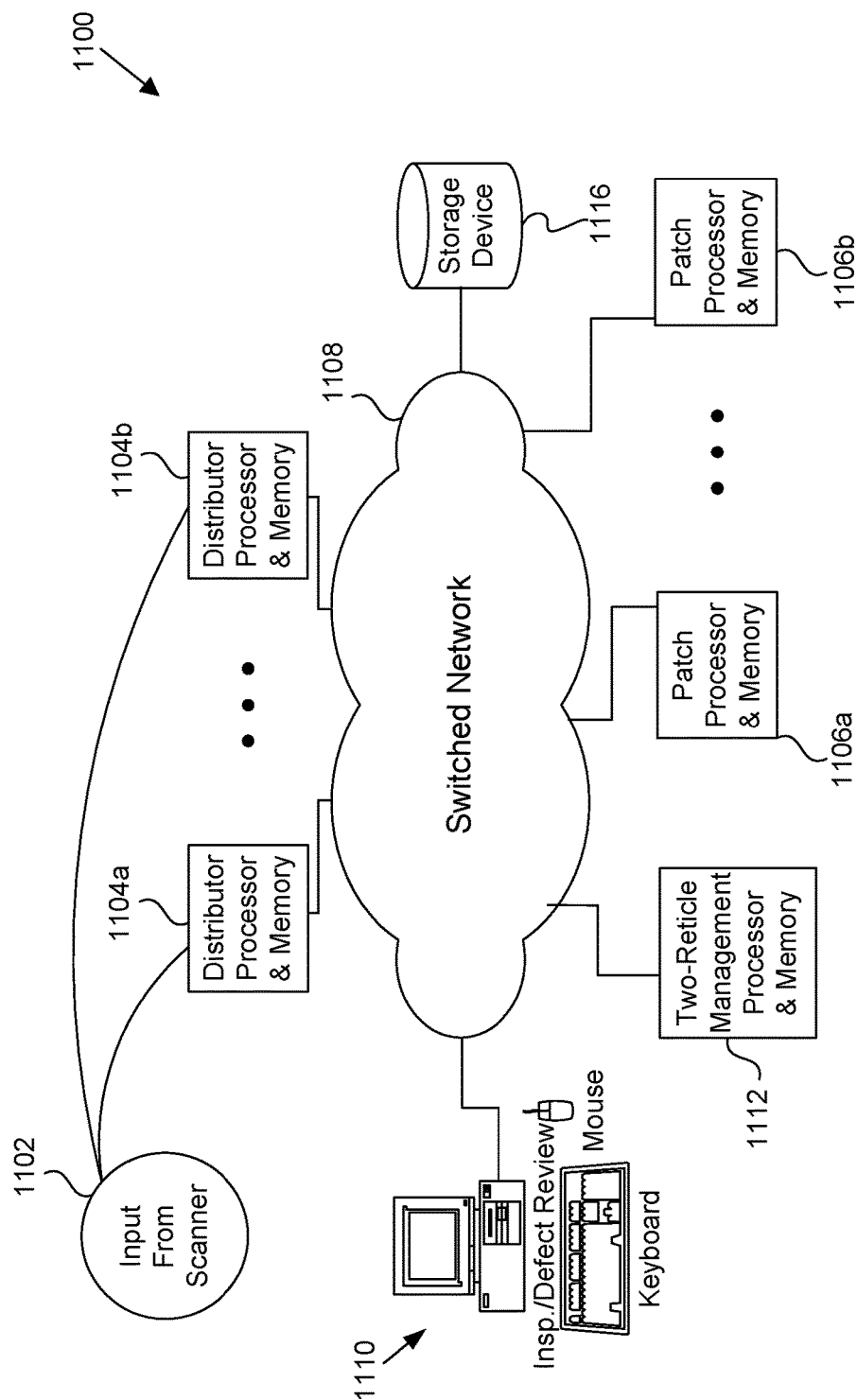
FIG. 11 is a diagrammatic representation of an example inspection system in which techniques of the present invention may be implemented

Techniques of the present invention may be implemented in any suitable combination of hardware and/or software. FIG. 11 is a diagrammatic representation of an example inspection system 1100 in which techniques of the present invention may be implemented. The inspection system 1100 may receive input 1102 from an inspection tool or scanner (not shown). Intensity values or images for each reticle may be obtained using an inspection tool that is set up in any suitable manner. The tool is generally set up with a set of operating parameters or a "recipe". Recipe settings may include one or more of the following settings: die extent, die array size, die offsets, a setting for scanning reticles in a particular pattern, pixel size, a setting for grouping adjacent signals from single signals, threshold values, a focus setting, an illumination or detection aperture setting, an incident beam angle and wavelength setting, a detector setting, a setting for the amount of reflected or transmitted light, aerial modeling parameters, etc.

The inspection tool may be generally operable to convert detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. The detected signals may also take the form of scanning electron microscope images or any other suitable type of images. A reticle image may also be generated after all the positions of the reticle are scanned and converted into detected signals, or portions of a reticle image may be generated as each reticle portion is scanned with the final reticle image being complete after the entire reticle is scanned.

The inspection tool may be setup in a high resolution imaging mode or an aerial imaging mode. That is, the detected signals may take the form of high resolution images or low resolution aerial images. In general, the optics of the photolithography tool are emulated so as to produce an aerial image based on the detected signals from the reticle. For instance, a NA (numerical aperture) for a high resolution mode is typically between about 0.5 and 0.9, while a NA for an aerial imaging (low resolution) mode is typically between about 0.1 and 0.35.

There may be some advantages to operating in the aerial imaging mode for more accurate use of the delta map implemenation for CD correction methods, such as the DoseMapper™ methodology available from ASML of Veldhoven, the Netherlands and the CDC correction methodology available from Zeiss of Germany. The delta value, $\Delta I/I$, is related to the fractional dose correction, $\Delta D/D$, by $\Delta I/I = -\Delta D/D$. This relationship may be more accurately correct for aerial inspection modes than for high resolution modes, but may suffice in both modes.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data for the detected signals for each set of one or more patches may be sent to parallel patch processors. For instance, the inspection system 1100 of FIG. 11 may also include a data distribution system (e.g., 1104a and 1104b) for distributing the received input 1102, an intensity/image signal processing system (e.g., patch processors and memory 1106a and 1106b) for processing specific portions/patches of received input 1102, a two-reticle management system (e.g., 1112) for managing any of the two reticle processes described herein, a network (e.g., switched network 1108) for allowing communication between the inspection system components, an optional mass storage device 1116 and one or more inspection control and/or review stations (e.g., 1110) for reviewing the candidate defects. The mass storage device 1116 may also be utilized for storing images from a first reticle that are then "played" back and compared to images that are received from a second reticle. Each processor of the inspection system 1100 typically may include one or more microprocessor integrated circuits and may also contain interface and/or memory integrated circuits and may additionally be coupled to one or more shared and/or global memory devices.

The scanner or data acquisition system (not shown) for generating input data 1102 may take the form of any suitable instrument (e.g., as described further herein) for obtaining intensity signals or images of a reticle (or other specimen). For example, the scanner may construct an optical image or generate intensity values of a portion of the reticle based on a portion of detected light that is reflected, transmitted, or otherwise directed to one or more light sensors. The scanner may then output the intensity values or image from the scanner.

Intensity or image data 1102 can be received by data distribution system via network 1108. The data distribution system may be associated with one or more memory devices, such as RAM buffers, for holding at least a portion of the received data 1102. Preferably, the total memory is large enough to hold at least an entire swath of data. For example, one gigabyte of memory works well for a swath of patches that is 1 million by 1000 pixels or points.

The data distribution system (e.g., 1104a and 1104b) may also control distribution of portions of the received input data 1102 to the processors (e.g. 1106a and 1106b). For example, data distribution system may route data for a first patch to a first patch processor 1106a, and may route data for a second patch to patch processor 1106b. Multiple sets of data for multiple patches may also be routed to each patch processor.

The patch processors may receive intensity values or an image that corresponds to at least a portion or patch of the reticles. The patch processors may each also be coupled to or integrated with one or more memory devices (not shown), such as DRAM devices that provide local memory functions, such as holding the received data portion.

Each set of input data 1102 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 1106a, and the second memory partition may hold and route second data to patch processor 1106b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s). Of course, two first patches from both reticle images may be routed to each processor for analysis together.

Figure 12A:
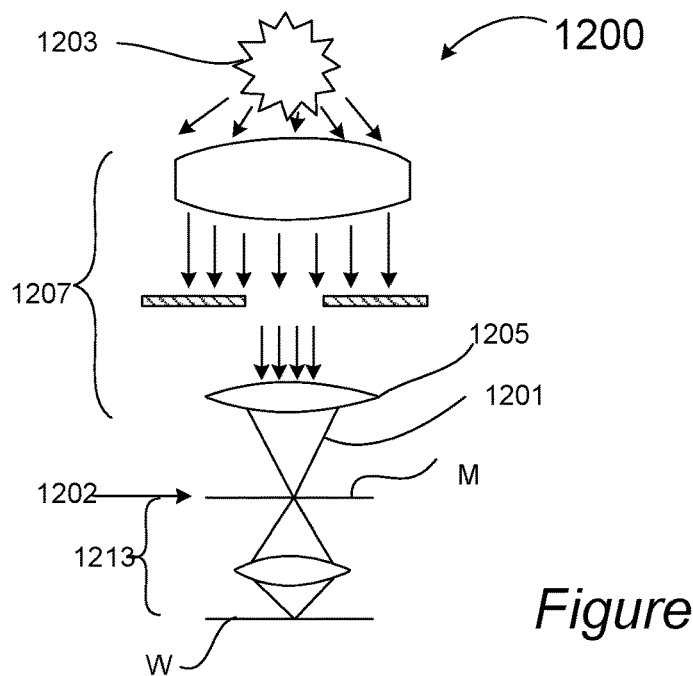
FIG. 12A is a simplified schematic representation of a lithographic system for transferring a mask pattern from a photomask onto a wafer in accordance with certain embodiments.

FIG. 12A is a simplified schematic representation of a typical lithographic system 1200 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 1203 directs a light beam through an illumination optics 1207 (e.g., lens 1205) onto a photomask M located in a mask plane 1202. The illumination lens 1205 has a numeric aperture 1201 at that plane 1202. The value of the numerical aperture 1201 impacts which defects on the photomask are lithographic significant defects and which ones are not. A portion of the beam that passes through the photomask M forms a patterned optical signal that is directed through imaging optics 1213 and onto a wafer W to initiate the pattern transfer.

Figure 12B:
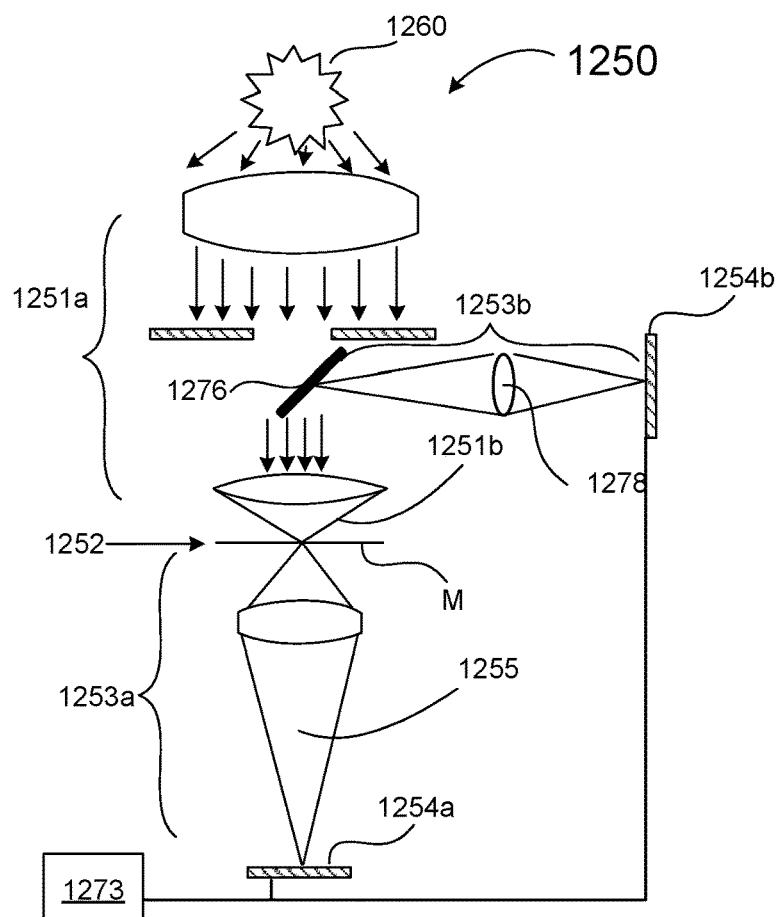
FIG. 12B provides a schematic representation of a photomask inspection apparatus in accordance with certain embodiments.

FIG. 12B provides a schematic representation of an example inspection system 1250 that has illumination optics 1251a includes an imaging lens with a relative large numerical aperture 1251b at a reticle plane 1252 in accordance with certain embodiments. For example, the numerical aperture 1251b at the reticle plane 1252 of the inspection system may be considerable greater than the numerical aperture 1201 at the reticle plane 1202 of the lithography system 1200, which would result in differences between test inspection images and actual printed images.

The depicted inspection system 1250 includes detection optics 1253a and 1253b, including microscopic magnification optics designed to provide, for example, 60-200× magnification or more for enhanced inspection. The inspection techniques described herein may be implemented on various specially configured inspection systems, such as the one schematically illustrated in FIG. 12B. The illustrated system 1250 includes an illumination source 1260 producing a light beam that is directed through illumination optics 1251*a* onto a photomask M in the reticle plane 1252. As explained above, the inspection system 1250 may have a numerical aperture 1251*b* at the reticle plane 1252 that may be greater than a reticle plane numerical aperture (e.g., element 1201 in FIG. 12A) of the corresponding lithography system. The photomask M to be inspected is placed on a mask stage at the reticle plane 1252 and exposed to the source.

The patterned image from the mask M is directed through a collection of optical elements 1253*a*, which project the patterned image onto a sensor 1254*a*. In a reflecting system, optical elements (e.g., beam splitter 1276 and detection lens 1278) direct and capture the reflected light onto sensor 1254*b*. Suitable sensors include charged coupled devices (CCD), CCD arrays, time delay integration (TDI) sensors, TDI sensor arrays, photomultiplier tubes (PMT), and other sensors.

The illumination optics column may be moved relative to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 1254*a* and/or 1254*b*) can be processed by a computer system 1273 or, more generally, by one or more signal processing devices, which may each include an analog-to-digital converter configured to convert analog signals from each sensor into digital signals for processing. The computer system 1273 typically has one or more processors coupled to input/output ports, and one or more memories via appropriate buses or other communication mechanisms.

The computer system 1273 may also include one or more input devices (e.g., a keyboard, mouse, joystick) for providing user input, such as changing focus and other inspection recipe parameters. The computer system 1273 may also be connected to the stage for controlling, for example, a sample position (e.g., focusing and scanning) and connected to other inspection system components for controlling other inspection parameters and configurations of such inspection system components.

The computer system 1273 may be configured (e.g., with programming instructions) to provide a user interface (e.g., a computer screen) for displaying resultant intensity values, images, and other inspection results. The computer system 1273 may be configured to analyze intensity, phase, and/or other characteristics of reflected and/or transmitted sensed light beam. The computer system 1273 may be configured (e.g., with programming instructions) to provide a user interface (e.g., on a computer screen) for displaying resultant intensity values, images, and other inspection characteristics. In certain embodiments, the computer system 1273 is configured to carry out inspection techniques detailed above.

Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, flash drive, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured Theron™ 6XX DUV inspection system available from KLA-Tencor of Milpitas, Calif.

For any of the above described embodiments, any suitable inspection tool may be used to obtain images of one or both same-design reticles. By way of examples, one or more of the following tools may be used: any type of charged particle beam tool (e.g., imaging electron microscope, scanning electron or ion microscope, such as a Helium ion microscope), electromagnetic inspection or coherent diffraction imaging tool, EUV inspection tool, scanning tunneling microscope (STM), atomic force microscope (AFM), actinic microscope, etc. Any of these tools may include one or more incident and collection channels so that two or more beams can simultaneously impinge on two or more reticles to efficiently obtain multiple images of multiple reticles.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
    loading, into one or more inspection tools, a first and second reticle that were fabricated with a same design;
    with the one or more inspection tools, acquiring a first and second reticle image from of the first and second reticles while loaded in the one or more inspection tools;
    comparing the first reticle image to the second reticle image to output a difference image having a plurality of difference events corresponding to candidate defects on either the first or second reticle; and
    generating an inspection report of the candidate defects.

2. The method of claim 1, wherein the first and second reticle images are acquired in a same inspection tool by loading the first and second reticles together into such inspection tool.

3. The method of claim 2, further comprising correcting the first and second reticle images for focus differences and/or light level differences of same locations on both the first and second reticles prior to comparing such first and second reticle images.

4. The method of claim 1, wherein the first and second reticle images are acquired in a same inspection tool by successively loading the first and second reticles into such inspection tool one after the other.

5. The method of claim 4, further comprising correcting the first and second reticle images for focus differences and/or light level differences for same locations on both the first and second reticles prior to comparing such first and second reticle images.

6. The method of claim 1, wherein the first and second reticle images are acquired by different inspection tools, the method further comprising correcting the first and second reticle images for tool parameter differences that affect same locations of the first and second reticle images prior to comparing such first and second reticle images.

7. The method of claim 1, wherein comparing the first reticle image to the second reticle image to output a difference image comprises:
    for each of a plurality of patches of each of the first and second reticle images, determining an average or mean intensity value for a plurality of locations in each patch; and
    comparing each patch's average or mean intensity value from the first reticle image to a corresponding one of the patch's average or mean intensity value at a same location in the second reticle to obtain a plurality of difference average or mean intensity values, which are analyzed to determine whether such difference average or mean intensity values are to be defined as candidate defects.

8. The method of claim 7, further comprising correlating the difference average or mean intensity values to critical dimension (CD) variations.

9. The method of claim 1, wherein the first and second reticles each include a single die.

10. The method of claim 1, further comprising:
    performing a cell-to-cell inspection on the first reticle image prior to comparing the first and second reticle images; and
    eliminating regions of the first and second reticle images that passed the cell-to-cell inspection from being compared to each other.

11. The method of claim 1, where the first reticle is newly manufactured and has not been used in a photolithography process, and the second reticle has been used in a photolithography process.

12. The method of claim 1, wherein the first and second reticles are both new and have not been used in a photolithography process, wherein the candidate defects found for the first and second reticles when they are new are defined as baseline events, the method further comprising:
    after the baseline events are defined, using one or both first and second reticles in a photolithography process; and
    repeating the operations for acquiring a first and second reticle image and comparing such first and second images after the first or second reticle has been used by excluding any resulting difference events that match the baseline events from the inspection report.

13. The method of claim 1, wherein the first and second reticles each include a plurality of dies having optical proximity correction (OPC) structures that differ between at least some of the dies.

14. An inspection system for inspecting photolithographic reticles, the system comprising at least one memory and at least one processor that are configured to perform the following operations:
    into one or more inspection tools of the inspection system, receiving a first and second reticle that were fabricated with a same design;
    with the one or more inspection tools, acquiring a first and second reticle image from the first and second reticles while loaded in the one or more inspection tools;
    comparing the first reticle image to the second reticle image to output a difference image having a plurality of difference events corresponding to candidate defects on either the first or second reticle; and
    generating an inspection report of the candidate defects.

15. The system of claim 14, wherein the inspection system includes a single inspection tool and the first and second reticle images are acquired in the single inspection tool by loading the first and second reticles together into such inspection tool.

16. The system of claim 15, wherein the at least one memory and at least one processor are further configured for correcting the first and second reticle images for focus differences and/or light level differences of same locations on both the first and second reticles prior to comparing such first and second reticle images.

17. The system of claim 14, further comprising at least one storage device, and wherein the inspection system includes a single inspection tool, wherein the first and second reticle images are acquired in the single inspection tool by successively loading the first and second reticles into such inspection tool one after the other, wherein the first reticle image is stored in and played back from the at least one storage device during the comparing operation.

18. The system of claim 17, wherein the at least one memory and at least one processor are further configured for correcting the first and second reticle images for focus differences and/or light level differences for same locations on both the first and second reticles prior to comparing such first and second reticle images.

19. The system of claim 14, wherein the inspection system includes different inspection tools and at least one storage device, wherein the first and second reticle images are acquired by the different inspection tools, the at least one memory and at least one processor being further configured for correcting the first and second reticle images for tool parameter differences that affect same locations of the first and second reticle images prior to comparing such first and second reticle images, wherein the first reticle image is stored in and played back from the at least one storage device during the comparing operation.

20. The system of claim 14, wherein comparing the first reticle image to the second reticle image to output a difference image comprises:
    for each of a plurality of patches of each of the first and second reticle images, determining an average or mean intensity value for a plurality of locations in each patch; and
    comparing each patch's average or mean intensity value from the first reticle image to a corresponding one of the patch's average or mean intensity value at a same location in the second reticle to obtain a plurality of difference average or mean intensity values, which are analyzed to determine whether such difference average or mean intensity values are to be defined as candidate defects.

21. The system of claim 20, wherein the at least one memory and at least one processor are further configured for correlating the difference average or mean intensity values to critical dimension (CD) variations.

22. The system of claim 14, the at least one memory and at least one processor further configured for comparing each patch's average or mean intensity value from the first reticle image to a plurality of corresponding ones of the patches' average or mean intensity value at a same location in the first reticle and the second reticle to obtain a plurality of difference average or mean intensity values, which are analyzed to determine whether such difference average or mean intensity values are to be defined as candidate defects.

23. The system of claim 14, wherein the first and second reticles each include a single die.

24. The system of claim 14, wherein the at least one memory and at least one processor are further configured for:
  performing a cell-to-cell inspection on the first reticle image prior to comparing the first and second reticle images; and
  eliminating regions of the first and second reticle images that passed the cell-to-cell inspection from being compared to each other.

25. The system of claim 14, where the first reticle is newly manufactured and has not been used in a photolithography process, and the second reticle has been used in a photolithography process.

26. The system of claim 14, wherein the first and second reticles are both new and have not been used in a photolithography process, wherein the candidate defects found for the first and second reticles when they are new are defined as baseline events, wherein the at least one memory and at least one processor are further configured for:
  after the baseline events are defined and after then using one or both first and second reticles in a photolithography process, repeating the operations for acquiring a first and second reticle image and comparing such first and second images after the first or second reticle has been used by excluding any resulting difference events that match the baseline events from the inspection report.

27. The system of claim 14, wherein the first and second reticles each include a plurality of dies having optical proximity correction (OPC) structures that differ between at least some of the dies.

28. A computer readable medium having instruction stored thereon for performing the following operations:
  loading, into one or more inspection tools, a first and second reticle that were fabricated with a same design;
  with the one or more inspection tools, acquiring a a first and second reticle image from the first and second reticles while loaded in the one or more inspection tools;
  comparing the first reticle image to the second reticle image to output a difference image having a plurality of difference events corresponding to candidate defects on either the first or second reticle; and
  generating an inspection report of the candidate defects.

* * * * *